United States Patent [19]
Kuwano et al.

[11] Patent Number: 5,629,340
[45] Date of Patent: May 13, 1997

[54] ANGIOGENESIS INHIBITOR AND NOVEL COMPOUND

[75] Inventors: Michihiko Kuwano; Mayumi Ono, both of Fukuoka; Mika Kusano, Chiyoda-ku; Junko Watanabe; Masakazu Takeda, both of Ami-machi, all of Japan

[73] Assignee: Tsumura & Co., Japan

[21] Appl. No.: 481,465

[22] PCT Filed: Dec. 27, 1993

[86] PCT No.: PCT/JP93/01893

§ 371 Date: Jul. 10, 1995

§ 102(e) Date: Jul. 10, 1995

[87] PCT Pub. No.: WO94/15594

PCT Pub. Date: Jul. 21, 1994

[30] Foreign Application Priority Data

Jan. 11, 1993 [JP] Japan .................. 5-002821

[51] Int. Cl.⁶ .................. A61K 31/34; A61K 31/05; A61K 31/075
[52] U.S. Cl. .................. 514/461; 514/720; 514/733; 549/499; 549/500; 549/501; 549/502; 549/562
[58] Field of Search .................. 514/461, 720, 514/733

[56] References Cited

U.S. PATENT DOCUMENTS

| | | | |
|---|---|---|---|
| 4,539,332 | 9/1985 | Biftu et al. | 514/461 |
| 4,595,693 | 6/1986 | Biftu et al. | 514/461 |

FOREIGN PATENT DOCUMENTS

| | | |
|---|---|---|
| 53-127812 | 11/1978 | Japan . |
| 2-142723 | 5/1990 | Japan . |
| 2-145513 | 6/1990 | Japan . |
| 2-180846 | 7/1990 | Japan . |

OTHER PUBLICATIONS

Pharmazie,, vol. 23, No. 3 (1968), Dann, O. et al, "Cetylcholire, XII. 3,4–Diphenylthiophere–2,5–Dicarboxylic Acid Bis[C. Beta.–Diethylaminolethyl Ester Methiodide]," pp. 135–145.

Vol. 72, No. 23 "Chemical Abstracts" Jun. 8, 1970.

J. Org. Chem., vol. 37, No. 26 (1972), Derry et al; 'Synthesis of Lighans, I. Norihydroquaiaretic Acid'; pp. 188–196.

J. Org. Chem., vol. 43, No. 2 (1978), Vedejs, E. et al "Transition–Metalperoxide Reactions." pp. 188–196.

J. Chem. Soc., Perkin Trans, vol. 1, No. 9, (1979), Biftu, Tesfaye et al "Synthesis of (.+–.)–deoxyschizanddrin." pp. 2276–2281.

(List continued on next page.)

*Primary Examiner*—Joseph E. Evans
*Attorney, Agent, or Firm*—Nixon & Vanderhye

[57] ABSTRACT

An angiogenesis inhibitor comprising, as an active agent, Compound (I) represented by the formula below:

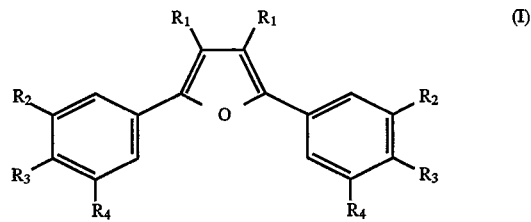

where $R_1$ is a lower alkyl group, an alkoxycarbonyl group or a carboxyl group; and $R_2$, $R_3$ and $R_4$ maybe the same or different and represent a hydrogen atom, a hydroxyl group, a methoxy group or an acetoxy group.

This compound has a remarkable angiogenesis inhibition activity, and an angiogenesis inhibitor useful for treatment of various diseases are provided.

4 Claims, 1 Drawing Sheet

OTHER PUBLICATIONS

Synthesis, vol. 12 (1983), Lapage, lucette et al "A Convenient Preparation of 1,4–dicarbonyl compounds by Ring Eleavage of Furans With Cerium (IV) Ammonium Nitratae" pp. 1018–1019.

Electrochim. Acta., vol. 30, No. 9, (1985), Barba, F. et al "Cathodic Reduction of .alpha.–bromopropiophenone In An Aprotic Mediu,." pp. 1119–1120.

J. Nat. Prod., vol. 53, No. 2, (1990), Kanno, Chohachi, Et al "Furanoid Lignans From Larrea Tridentate." pp. 396–406.

ANGIOGENESIS INHIBITOR AND NOVEL COMPOUND

This application is a 371 of PCT/JP93/01893 Dec. 27, 1993.

TECHNICAL FIELD

The present invention relates to an angiogenesis inhibitor and a novel compound for use therein.

PRIOR ART

While angiogenesis(vascularization) is known to occur in normal physiological states of human beings or animals, such as germinal occurrence and ovulocycle and placentationa in female estrus cycle, and to occur in healthy and normal physiological states such as wound healing and restration processes of inflammations and the like, it is known to occur in a wide variety of pathological states accompanying a rapid increase or expansion of blood capillaries which will cause serious damage to tissues. For example, as described in N. English. J. Med. 285: 1182, 1971, that tumor growth is dependent on the increase in the angiogenesis of the tumor tissue. Mastubara et al. also report, in Inflammation, Vol. 10, No. 4, July 1990, p 241–245, that there is a correlation between the neogenesis of small blood vessels, such as capillaries and postcapillary venules, and the cellular infiltration of monocytes and lymphocytes in inflammatory processes, and that the neogenesis of the small blood vessels serving as a nutrition-supply blood vessel is indispensable for growth of proud flesh.

Other examples of the disorders associated with abnormal acceleration of angiogenesis, ophthalmological diseases such as diabetic retinitis, retrolental fibroplasia, angiogenesis associated with corneal implantation, glaucoma, eye tumor, and trachoma; pediatric diseases such as angioma and fibrous angioma; surgical disorders such as hypertrophic scar and proud flesh; diseases of internal medicine such as rheumatoid arthritis and edematous sclerosis; and a heart disease such as atherosclerosis; and various types of tumors.

Recently, attention has been paid to angiogenesis inhibitor, which may be used in pharmaceuticals for treating the various types of disorders mentioned above. A drug having an anti-angiogenic activity is useful for the treatment of various diseases, during whose pathological processes, it is known that the neogenesis of small blood vessels occurs. These diseases contain, for example, a cancer, a chronic inflammation such as chronic articular rheumatism, diabetic retinitis, prematurity retinitis, various thrombotic disorders in a retina, arteriosclerosis, angioma, fibrous angioma and psoriasis.

As one of drugs having an anti-angiogenic activity, tetrahydrocortizol is disclosed in Inflammation (Vol. 10, No. 4, July 1990, p 241–245) described above. It is also disclosed that some of the anti-rheumatoid agents used in chronic articular rheumatism treatment have the anti-angiogenic activity. Examples of the antirheumatoid agents include SH compounds such as aurothiomaleate sodium, auranofin and D-penicillamine.

However, the drugs having the anti-angiogenic activity have various clinical problems. For example, to express the anti-angiogenic activity, tetrahydrocortizol must be applied together with heparin having an angiogenesis accelerating activity.

On the other hand, Most of the aforementioned antirheumatoid agents having the anti-angiogenic activity have serious side effects. They can hardly be applied in view of control of drug administration.

The present invention was made on the basis of the aforementioned circumstances and provides an angiogenesis inhibitor having a remarkable antiangiogenic activity and useful for treatment and protection of various diseases accompanying abnormal acceleration of angiogenesis, and provides a novel compound having the anti-angiogenic activity.

DISCLOSURE OF THE INVENTION

The present inventors made intensive studies with a view toward solving the above-mentioned problems. As a result, they found a remarkable anti-angiogenic activity in lignans which they have previously described in Jpn. Pat. Appln. KOKAI Publication No. 2-180846, provided by the present applicant, and will be described later. They investigated further into the compounds having an anti-angiogenic activity. As a result, they newly found a novel compound having the anti-angiogenic activity, thereby accomplishing the present invention.

More specifically, the present invention provides an angiogenesis inhibitor comprising, an active ingredient, any one of the following compounds or a mixture consisting of at least two compounds selected from the following compounds:

Compound I represented by general formula (I) below:

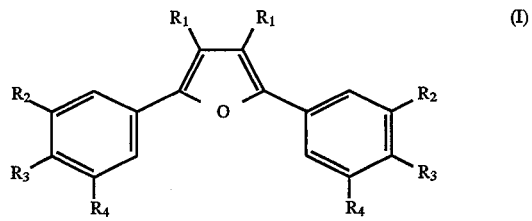

wherein $R_1$ is a lower alkyl group having 1 to 4 carbon atoms, an alkoxycarbonyl group having 1 to 4 carbon atoms in the alkoxy moiety or a carboxyl group; and $R_2$, $R_3$ and $R_4$ may be the same or different and each represents a hydrogen atom, a hydroxyl group, a methoxy group or an acetoxy group, wherein $R_2$ and $R_3$ may bind together to close a ring as shown in general formula (II) below:

where m is an integer from 1 to 6;

Compound III represented by general formula (III) below:

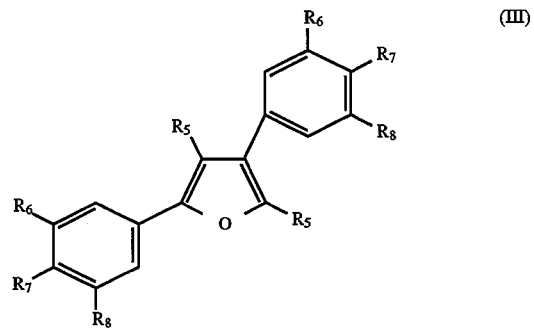

where

R$_5$ is a lower alkyl group having 1 to 4 carbon atoms; and

R$_6$, R$_7$ and R$_8$ may be the same or different and each represents a hydrogen atom, a hydroxyl group, a methoxy group or an acetoxy group; and Compound IV represented by general formula (IV) below:

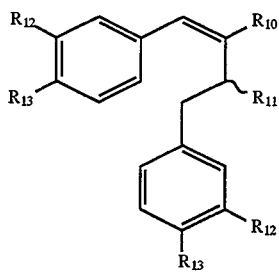 (IV)

where R$_{10}$ and R$_{11}$ may be the same or different and each represents a lower alkyl group having 1 to 4 carbon atoms; and R$_{12}$ and R$_{13}$ may be the same or different and each represents a hydroxyl group or a methoxy group.

Further, the present invention provides a novel compound represented by general formula (V) below:

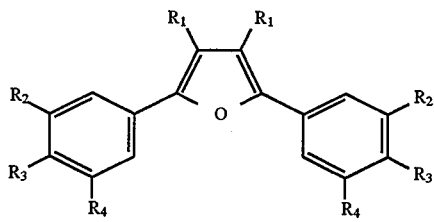 (V)

wherein R$_1$ represents a lower alkyl group having 1 to 4 carbon atoms, an alkoxycarbonyl group having 1 to 4 carbon atoms in the alkoxy moiety, or a carboxyl group; and R$_2$, R$_3$ and R$_4$ may be the same or different and each represent a hydrogen atom, a hydroxyl group, a methoxy group or an acetoxy group, wherein R$_2$ and R$_3$ may bind together to close the ring as shown in general formula (II) below:

 (II)

where m is an integer from 1 to 6; except that R$_1$ to R$_4$ have the combination listed in Table 1

TABLE 1

| COMPOUND | R$_1$ | R$_2$ | R$_3$ | R$_4$ |
|---|---|---|---|---|
| A | Methyl | Methoxy | Hydroxyl | Hydrogen atom |
| B | Methyl | Methoxy | Methoxy | Hydrogen atom |
| C | Methyl | Hydroxyl | Hydroxyl | Hydrogen atom |
| D | Methyl | Methoxy | Acetoxy | Hydrogen atom |
| E | Methyl | Hydroxyl | Methoxy | Hydrogen atom |

The present invention further provides a novel compound represented by general formula (III) below:

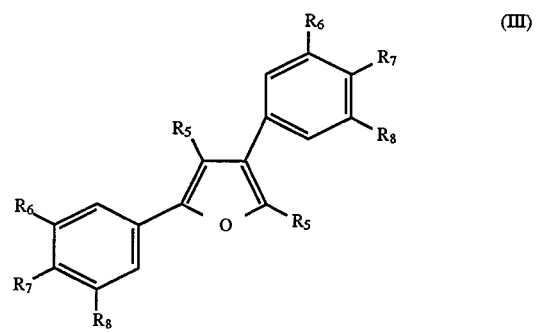 (III)

where

R$_5$ is a lower alkyl group having 1 to 4 carbon atoms; and

R$_6$, R$_7$ and R$_8$ may be the same or different and each represents a hydrogen atom, a hydroxyl group, a methoxy group or an acetoxy group.

Hereinbelow, the present invention! will be explained in detail.

The compounds represented by Formulas (I), (III) and (IV) are referred to as, for convenience, Compounds I, III and IV, respectively.

Of compounds of Compound I serving as one of active ingredients of the angiogenesis inhibitor of the present invention, the compounds whose R$_1$ to R$_4$ in general formula (I) are consisting of the combinations shown in Table 1 (hereinafter the compounds on he 1st line to the 4th line of Table 1 will be referred to as "Compounds A to E consecutively) are extraction component A from a guaiac resin (resin of Guaiacum Officinale L) and derivatives thereof, B to E, disclosed in Jpn. Pat. Appln. KOKAI Publication No. 2-180846. The aforementioned KOKAI publication discloses that Compounds A to E have 5-lipoxygenase inhibition and aldosereductase inhibition, but does not refer to an anti-angiogenic activity at all.

Compound I can be synthesized, for example, in the following manner.

Compound VI represented by general formula (VI), which can be obtained in accordance with a method described in, for example, ORGANIC PREPARATIONS AND PROCEDURES INT, 8 (IV), 179–183 (1976) and SYNLETT, 421–423 (1990), is used as a starting material.

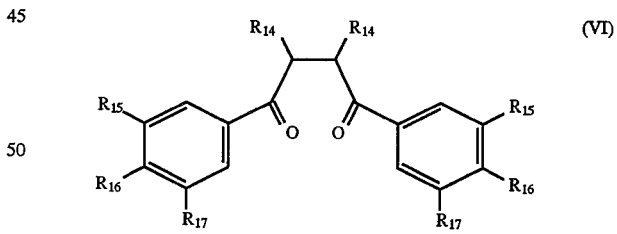 (VI)

where, R$_{14}$ represents a lower alkyl group having 1 to 4 carbon atoms, an alkoxycarbonyl group having 1 to 4 carbon atoms in the alkoxy moiety or a carboxyl group; R$_{15}$, R$_{16}$ and R$_{17}$ may be the same or different and each represents a hydrogen atom, a methoxy group or a benzyloxy group.

Compound I may be obtained by condensation between the 1-position and the 4-position carbon atoms of the butane portion of Compound VI. If necessary, other compounds I can be derived by removing methyl or benzyl group or alkylation of R$_{14}$ to R$_{16}$, after the condensation reaction of the compound VI.

The condensation reaction herein can be performed by heating Compound VI or a derivative thereof in an inorganic acid such as hydrochloric acid or sulfuric acid; an organic acid such as p-toluenesulfonic acid or trifluoroacetic acid; or a Lewis acid such as aluminum chloride or boron trifuluoride ether complex. Also, the condensation reaction of Compound VI may be performed by heating Compound VI together with a dehydration agent such as phosphorus pentaoxide, acetic anhydride or acetyl chloride in an appropriate solvent.

The removing of benzyl group is performed when a benzyloxy group is converted to a hydroxyl group and can be carried out, for example, in an appropriate organic solvent under a hydrogen atmosphere, using a catalyst such as Raney nickel, nickel boride, palladium hydroxide, palladium chloride, palladium black or palladium carbon.

The removing of methyl group is performed when a methyl group or a methoxy group is converted to a hydrogen atom or a hydroxyl group, respectively. The removing of methyl group can be carried out by reacting Compound VI with a Lewis acid (for example, boron chloride) in a halogenated hydrocarbon (for example, dichloromethane and chloroform) or an aromatic hydrocarbon.

The alkylenation is performed when hydrogen atoms which are adjacent each other are alkylenated to be crosslinked. The alkylenation is carried out by reacting Compound VI with an alkylene dihalide (e.g., ethylene dibromide, methylene dibromide, methylene diiodide, bromochloromethane and dichlromethane) in a solvent such as acetone or dimethylformamide in the presence of a base such as potassium carbonate.

The reaction solution obtained in each synthesis step may be purified if necessary and Used in the following step. For example, the reaction solution, after being dried or as it is, is first subjected to column chromatography using an absorbent such as a silica gel, an ODS-silica gel, a porous polymer gel or Sephadex, and an eluant are fractionated to obtain fractions. Usable elution solvents in the column chromatography include water, methanol ethanol, acetone, ethyl acetate, tetrahydrofuran (THF), acetonitrile, benzene, ether, dichloromethane, chloroform, petroleum ether, hexane, cyclohexane and the like, which are used in a single or as a mixed solvent of at least two solvents.

The thus obtained fractions are subjected to recrystallization or pulverization using a solvent such as water, methanol, ethanol, acetone, ethyl acetate, THF, acetonitrile, benzene, ether, chloroform, dichloromethane, petroleum ether or hexane, which may be used in a single or as a mixed solvent of at least two solvents, affording a desired pure product.

In addition to the aforementioned synthesis methods, Compound A of Compound I can be obtained by extracting and separating from a guaiac resin in accordance with an ordinary method. Other compounds of Compound I can be derived from Compound A in accordance With an ordinary method.

In general formula (I), $R_1$ of Compound I is preferably one selected from the group consisting of methyl, isobutyl, ethoxycarbonyl and carbonyl, more preferably methyl or ethoxycarbonyl, most preferably methyl.

Further, in general formula (I), $R_2$ of Compound I is preferably methoxy or a hydroxyl group. $R_3$ is preferably methoxy, a hydroxyl group or acetoxy. It is more preferable that both $R_2$ and $R_3$ are methoxy, or that if one of $R_2$ and $R_3$ is methoxy, and the other is a hydroxyl group. When both $R_2$ and $R_3$ are methoxy groups, it is preferable that these groups bind each other to close a ring. Furthermore, it is most preferable that one of $R_2$ and $R_3$ is methoxy and the other is a hydroxyl group.

It is further preferable that $R_4$ of Compound I is a hydrogen atom or methoxy and more preferably a hydrogen atom.

More preferable combination of $R_1$ to $R_4$ of Compound I is that $R_1$ is methyl, isobutyl or ethoxycarbonyl, one of $R_2$ and $R_3$ is methoxy, the other is hydroxyl group, and $R_4$ is a hydrogen atom or methoxy. The most preferable one of these combinations is that $R_1$ is methyl, one of $R_2$ and $R_3$ is methoxy, the other is a hydroxyl group; and $R_4$ is a hydrogen atom. However, when one of $R_2$ and $R_3$ is methoxy and the other is a hydroxyl group, $R_1$ and $R_4$ will not be particularly restricted if they fall within the scope of general formula (1) mentioned above.

Compound III as a second active ingredient of the present invention can be synthesized from compound (1) as a starting material, as shown in the following schema (I).

SCHEMA (I)

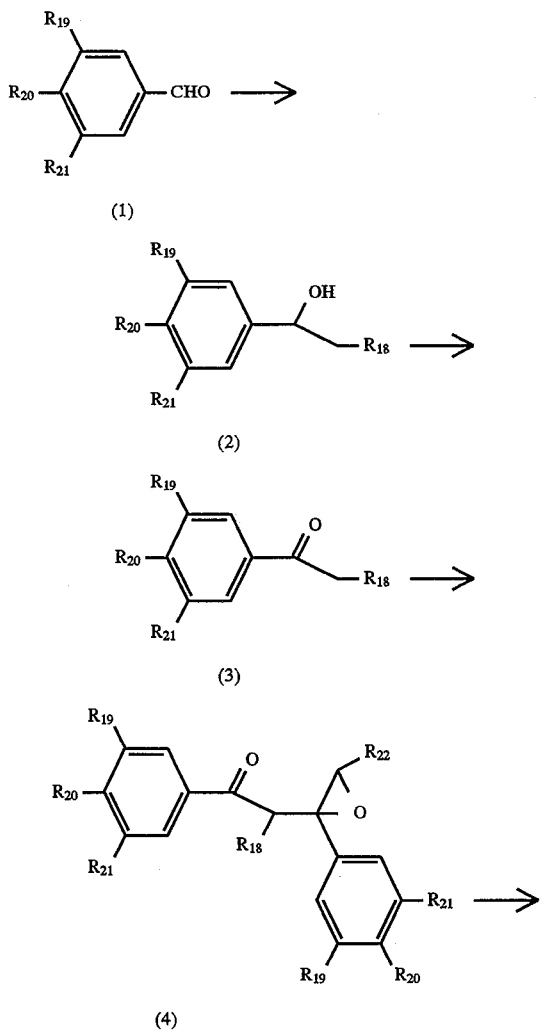

-continued
SCHEMA (I)

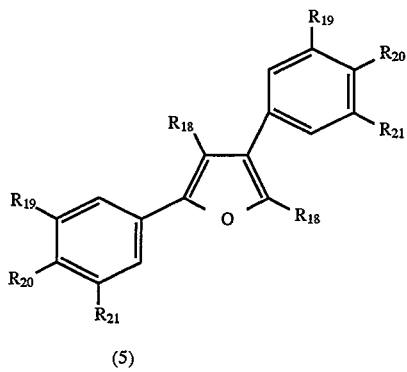

(5)

wherein, $R_{18}$ is a lower alkyl group having 1 to 4 carbon atoms, an alkoxycarbonyl group or a carboxyl group; and $R_{19}$, $R_{20}$ and $R_{21}$ are the same or different and each represents a hydrogen atom, a methoxy group or a benzyloxy group.

As compound (1), benzylvaniline (3-methoxy-4-hydroxybenzaldehyde), isovaniline, or syringaldehyde can be used.

When compound (1) has a hydroxyl group, the hydroxyl group is first protected with a suitable protecting group in accordance with an ordinary method, and compound (2) can be prepared. Examples of usable protecting groups of the hydroxyl group include a substituted or unsubstituted benzyl group such as benzyl, 4-methoxybenzyl, 4-nitrobenzyl, trityl or benzhydryl, and a silyl group such as t-butyldimethylsilyl, t-butyldiphenylsilyl, or triphenylsilyl.

In a case of the benzyl group, an introduction of the protecting group can be performed by, for example, reacting compound (1) with the corresponding benzyl halide or benzyl sulfonate in the presence of a base such as an alkaline metal carbonate, an alkaline metal hydroxide, or an alkaline metal hydride in a general solvent such as alcohol, dimethylformamide (DMF), dimethylsulfoxide (DMSO), tetrahydrofuran (THF), benzene or acetone; water or a mixed solvent of the aforementioned solvents, while cooling or heating. On the other hand, when the protecting group is the silyl group, the introduction can be performed by reacting compound (1) with the corresponding general silylation agent such as silyl halide or silyl sulfonate in the presence of an organic or an inorganic base such as an amine or an alkaline metal carbonate in an aprotic solvent such as DMF, DMSO, THF, dichloromethane ($CH_2Cl_2$), chloroform ($CHCl_3$) or benzene, while cooling or heating.

Subsequently, an alkyl group $CH_2 R_{18}$ is added to an aldehyde group of compound (2) to obtain compound (3). This addition reaction of the alkyl group can be carried out by reacting compound (2) with alkyl lithium, alkyl magnesium halide, or an alkyl metal corresponding to the alkyl group to be introduced, in an aprotic organic solvent such as THF, ether or benzene, while cooling or heating.

Thereafter, an alcoholic hydroxyl group of compound (3) is oxidized to obtain compound (4) For example, the oxidation reaction can be carried out by oxidizing the alcoholic hydroxyl group of compound (3) with a heavy metal salt such as chromic acids (e.g., PCC, anhydrous chromic acid, sodium dichromate, PDC, The Collins agent), manganese compounds (e.g., manganese dioxide, potassium permanganate), or ruthenium (e.g., tetrapropylammonium perruthenate), in a solvent such as acetone, benzene or dichloromethane, or by oxidizing the alcoholic hydroxyl group of compound (3) using an organic compound such as DMSO or NBS. However, the oxidation reaction is not restricted to the above-mentioned methods. Any methods used for the oxidation of alcohol can be applied.

Subsequently, compound (4) is dimerized to obtain compound (5). More specifically, compound (5) can be obtained by reacting compound (4) with α haloketone of compound (4) separately chlorinated, in the presence a basic compound such as lithium dialkylamide, sodium amide or potassium amide in a solvent such as THF or liquid ammonia, while cooling or heating. The α haloketone of compound (4) can be obtained by reacting compound (4) with chlorine or copper chloride, or with a chlorinating agent such as chlorine, N-chlorosuccinimide (NCS) in the presece of a base. In this way, condensation of compound(4) and its α haloketone affords compound(5) accompanied by the concomitant epoxy formation of the ketone portion of α haloketone .

By reacting compound (4) with the chlorinating agent in the presence of an excessive amount of the basic compound, halogenation and epoxidation can be carried out in one step.

Subsequently, the compound (5) is annulated to form the compound (6). The annularion of compound (5) is performed by reacting compound (5) with a general acid (e.g., hydrochloric acid, sulfuric acid, acetic acid, toluenesulfonic acid), a Lewis acid-(e.g., boron fluoride ether complex, aluminum chloride), or a dehydration agent such as, trifluoacetic anhydride, phosphorus pentaoxide in an appropriate solvent.

Thereafter, if an annulated compound has a protected hydroxyl group, the compound may be subjected to a deprotection reaction to obtain the compound (6). When the protecting group is a benzyl group, the deprotection reaction may be performed in the presence of a palladium catalyst (palladium-carbon, palladium hydroxide, palladium black, palladium chloride) in a hydrogen atmosphere or a general organic solvent (alcohol, ethyl acetate, benzene, THF) with stirring. On the other hand, when the protecting group is a silyl group, the deprotection reaction may be performed with an acid such as hydrochloric acid or a fluorine compound such as potassium fluoride, cesium fluoride, ammonium fluorides, hydrogen fluoride in an organic solvent such as acetonitrile, alcohol or THF.

Of compounds of Compound IV as a third active ingredient of the angiogenesis inhibitor of the present invention, a compound (hereinafter referred to as Compound F) whose $R_5$ is a methyl group, $R_6$ is α methyl group, $R_7$ is a methoxy group, and $R_8$ is a hydroxyl group, in the general formula (IV), is an extraction component from a guaiac resin similar to Compound A as disclosed in Jpn. Pat. Appln. KOKAI Publication No. 2-180846. Other Compound IV excluding Compound F can be derived from Compound F in accordance with an ordinary method.

Hereinbelow, the angiogenesis inhibition activity of the aforementioned Compounds I, III and IV (hereinafter, Compounds I, III and IV will be collectively referred to as "present compound(s)") will be explained.

An in-vitro angiogenesis models have been established, using human omental capillary endothelial cells (hereinafter referred to as "HOME cells"). One is the angiogenesis models in a process of wound healing formed when the HOME cells are damaged with a razor blade. Another one is a model of HOME cell migration, synthesis of a tissue plasminogen activation factor (t-PA), and HOME-cell tube formation, accelerated by $TGF_α$.

The present inventors have made studies regarding compounds having an angiogenesis inhibition activity, using the aforementioned two angiogenesis models. As a result, they found that Compounds A to F, which are guaiac resin extraction components, inhibit normal angiogenesis observed in the wound healing of the HOME cells. Furthermore, they found that novel compounds separately synthesized, such as Compound I excluding Compounds A to D, Compound III and Compound IV excluding compound E have the similar activity.

The present compounds inhibit the migration of the HOME cells, the t-PA synthesis, and the tube formation of the HOME cells, which are accelerated by $TGF_\alpha$. To be more surprised, these compounds may inhibit the angiogenesis induced by human cancer cells.

Likewise the present compounds are extremely useful for angiogenesis, in particular for improvement of the pathogenic process related with abnormal acceleration of angiogenesis. The present compounds can be used in, for example, suppressing tumor cell growth, curing of inflammation, and suppressing proud flesh growth. The present compounds can be expected to be widely applied to treatment of diseases correlated with angiogenesis.

The angiogenesis inhibitor of the present invention contains the aforementioned Compound I, Compound III or Compound IV, or a mixture thereof as an active ingredient. More specifically, the present compounds may be contained alone or a mixture of at least two compounds may be used. Further, the present compounds may be used together with a pharmaceutical acceptable carrier.

The administration form of the angiogenesis inhibitor of the present invention is not particularly restricted and can be appropriately selected according to requirements. The examples of the administration forms include peroral agents such as a tablet, capsule, granule, subtilized granule, powder and liquid preparation; and parenteral agents such as injection and suppository.

The angiogenesis inhibitor of the present invention may be orally administrated. In this case, the weight of the active ingredient of the angiogenesis inhibitor of the present invention varies depending on the age, gender, or weight of a patient, or the significance level of a disease. The dosage for an adult usually falls within the range of 30 to 1000 mg/day. It is preferred to administrate this dosage to a patient several times a day.

The peroral agent can be produced, using the present compounds alone or, using a diluent such as starch, lactose, sucrose, mannit (mannitol), carboxymethyl cellulose, corn starch or an inorganic salt, in accordance with an ordinary method. Other than the aforementioned diluents, an appropriate binder, disintegrant, surfactant, lubricant, flow ability-accelerating agent, corrigent, colorant or flavor may be selectively used.

The examples of the binders include starch, dextrin, gum-arabic powder, gelatin, hydroxy-propylstarch, methyl cellulose, sodium carboxylmethyl cellulose, hydroxypropyl cellulose, crystalline cellulose, ethyl cellulose, polyvinylpyrrolidone, and macrogol.

The examples of the disintegrants include starch, hydroxypropylstarch, sodium carboxymethyl cellulose, calcium carboxymethyl cellulose, carboxymethyl cellulose, and hydroxypropyl cellulose of a low-substitute rate.

The examples of the surfactants include sodium lauryl sulfate, soy-bean lecithin, sucrose fatty acid ester, and polysorbate 80.

The examples of the lubricants include talk, wax, hydrogenated vegetable oil, sucrose fatty acid ester, magnesium stearate, calcium stearate, aluminum stearate and polyethylene glycol.

The examples of the flow ability-accelerating agents include light anhydrous silicic acid, dried aluminum hydroxide gel, synthesized aluminum silicate and magnesium silicate.

Furthermore, the angiogenesis inhibitor of the present invention may be administrated in the form of a suspension, emulsion, syrup or elixir. In these forms, a corrigent and a colorant may be contained.

The angiogenesis inhibitor of the present invention can be parenterally administrated. In this case, the weight of the active ingredient of the angiogenesis inhibitor of the present invention varies depending on the age or weight of a patient, or the significance level of disease. The dosage for adults usually falls within the range of 1 to 300 mg/day. It is preferred to administrate this dosage to a patient by an intravenous injection, intravenous drip, subcutaneous injection or intramuscular injection.

The present compound can be parenterally administrated by diluting it with an appropriate diluent. The usable diluents include distilled Water for injection, saline, aqueous glucose solution, vegetable oil for injection, sesame oil, peanut oil, soybean oil, corn oil, propylene glycol and polyethylene glycol. To the parenteral agent, a disinfectant, preservative and stabilizer can be added if necessary.

Of these parenteral agents, particularly an injection agent may be preserved in a lyophilized form and used by returning a liquid-form again from the lyophilized form, just before use. The lyophilized form can be prepared by charging the injection agent in a vial and the like, freezing, and removing moisture by a generally-used lyophilization technique. To the injection agent, an isotonicity, stabilizer, preservative, soothing agent and the like may be added. The parenteral agents other than these agents include a paint such as a liquid for external use or an ointment, and a suppository for rectum administration. These parenteral agents can be produced according to an ordinary method.

As explained in the foregoing, the angiogenesis inhibitor of the present invention contains the present compound having an angiogenesis inhibition activity as an active ingredient and is extremely useful for improvement of the pathological process correlated with the angiogenesis. The angiogenesis inhibitor of the present invention can be used for, for example, suppressing tumor cells growth, curing inflammation, and suppressing proud flesh growth. Other than the above usages, the angiogenesis inhibitor of the present invention may also used in treatment for diseases correlated with angiogenesis To be more specific, the angiogenesis inhibitor of the present invention has the angiogenesis inhibition activity as well as the inhibition activity of abnormally accelerated angiogenesis observed in pathological processes. By virtue of these activities, extremely useful pharmaceutical agents in the treatment for various diseases accompanying the abnormally accelerated angiogenesis, represented by the treatment for suppression of tumor-cell growth and inflammation. The novel compound of the present invention is a useful compound having extremely remarkable effects as an ingredient of such an angiogenesis inhibitor.

BEST MODE OF CARRYING OUT THE INVENTION

Figure 1:
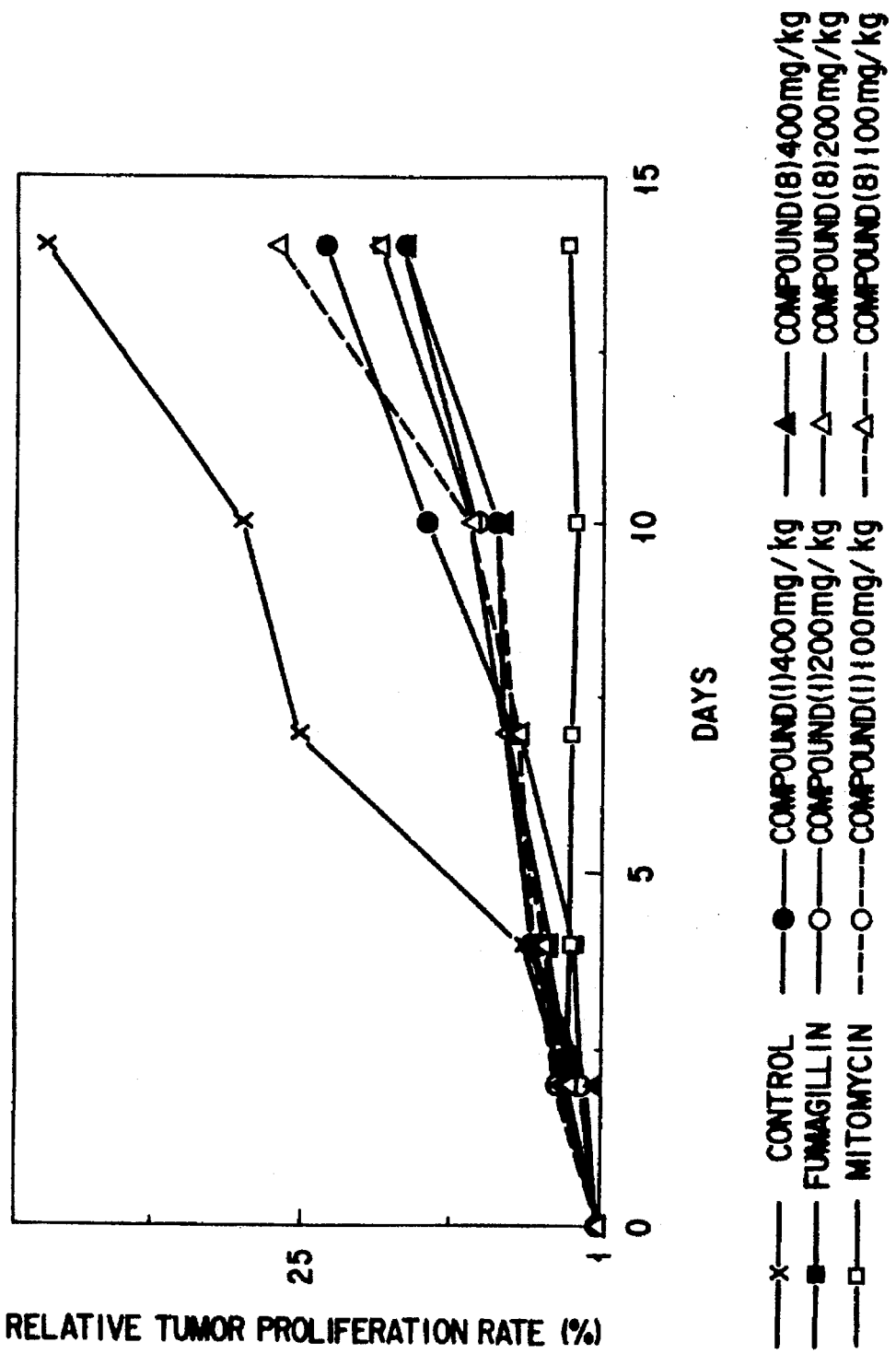
FIG. 1 is a graph showing the relative tumor growth rate versus days after the administration of drugs in Experiment 1.

Hereinbelow, the present invention will be explained in detail with reference to Examples, which should not be construed as limiting the scope of the present invention.

Prior to carrying out experiments or confirming the angiogenesis inhibition activity of the present invention, compounds (1) to (14) used for the experiments, shown in Tables 2 to 4 were obtained as described in Examples.

TABLE 2

General formula (I)

| COMPOUND | $R_1$ | $R_2$ | $R_3$ | $R_4$ |
|---|---|---|---|---|
| 1 | Methyl | Methoxy | Hydroxyl | Hydrogen atom |
| 2 | Methyl | Methoxy | Methoxy | Hydrogen atom |
| 3 | Methyl | Hydroxyl | Hydroxyl | Hydrogen atom |
| 4 | Methyl | Methoxy | Acetoxy | Hydrogen atom |
| 6 | Methyl | —O—CH$_2$—O— | | Hydrogen atom |
| 7 | Methyl | —O—(CH$_2$)$_2$—O— | | Hydrogen atom |
| 8 | Methyl | Hydroxyl | Methoxy | Hydrogen atom |
| 10 | Isobutyl | Methoxy | Hydroxyl | Hydrogen atom |
| 11 | Methyl | Methoxy | Hydroxyl | Hydroxyl |
| 12 | Ethoxy-carbonyl | Methoxy | Hydroxyl | Hydrogen atom |
| 13 | Isobutyl | Hydroxyl | Methoxy | Hydrogen atom |
| 14 | Carboxyl | Methoxy | Hydroxyl | Hydrogen atom |
| 15 | Ethoxy-carbonyl | Hydroxyl | Methoxy | Hydrogen atom |
| 16 | Carboxyl | Hydroxyl | Methoxy | Hydrogen atom |

TABLE 3

General formula (III)

| COMPOUND | $R_5$ | $R_6$ | $R_7$ | $R_8$ |
|---|---|---|---|---|
| 9 | Methyl | Methoxy | Hydroxyl | Hydrogen atom |

TABLE 4

General formula (IV)

| COMPOUND | $R_{10}$ | $R_{11}$ | $R_{12}$ | $R_{13}$ |
|---|---|---|---|---|
| 5 | Methyl | ($\alpha$)Methothyl | Methoxy | Hydroxyl |

EXAMPLES 1 TO 4

Compound (1) shown in Table 2 was synthesized in accordance with the synthesis method de scribed in *ORGANIC PREPARATIONS PROCEDURES INTERNATIONAL*.

Also, compounds (2) to (4) shown in Table 2 were derived from compound (1) obtained above, in accordance with an ordinary method.

EXAMPLE 5

Compound (5) shown in Table 3 was obtained by extraction and purification from a guaiac resin, in accordance with the method disclosed in Jpn. Pat. Appln. KOKAI Publication No. 2-180846.

EXAMPLE 6

3,4-dimethyl-2,5-bis(3,4-methylenedioxyphenyl)-furan as compound (6) shown in Table 2, was produced in the following manner:

At first, 50 mg of compound (1) obtained in Example 1 was dissolved in 1 ml of anhydrous dichloromethane. To this mixture, 0.9 ml of 0.8M boron trichloride was further added, and the mixture was stirred for 2 hours at room temperature. After the completion of the reaction was confirmed by thin-layer chromatography (TLC), water was added to the reaction solution and the precipitate generated was collected by filtration. This precipitate was dissolved in acetone and filtered, and the resultant filtrate was concentrated to dryness, affording 22.1 mg of 3,4-dimethyl-2,5-bis(3,4-dihydroxyphenyl)furan.

Subsequently, 12.2 g of 3,4-dimethyl-2,5-bis(3,4-dihydroxyphenyl)furan was dissolved in 290 ml of dimethylformamide. Then the inner air of the reaction vessel was replaced with argon gas. This operation was repeated three times. Thereafter, 40 g of anhydrous potassium carbonate was added to the reaction solution, the inner air of the reaction vessel was again replaced with argon gas three times. Afterward, to the reaction solution, 8.7 ml of dibromomethane was added, and the mixture was stirred for 4 hours at 60° C. After the completion of the reaction was confirmed by TLC, the reaction solution was diluted with ethyl acetate and washed with 2N hydrochloric acid, water, saturated sodium hydrogen carbonate and a brinebrine, in this order. Subsequently, the resultant solution was dried over anhydrous magnesium sulfate and the solvent was removed to dryness by distillation, affording of 9.76 g of residue. The residue obtained was subjected to silica gel column chromatography [column size:(diameter) 6 cm (diameter)×20 cm , Kiesel gel 60, 70–230 mesh, hexane-ethyl acetate (8:1), 15 ml/fraction]. The 33rd to 280th fractions were combined and concentrated, and recrystallized from ethyl acetate-hexane, affording 5.0815 g of compound (6).

Physicochemical properties of product (6) are as follows:
Description: colorless needle crystal
Melting point: 152°–153° C.
Infrared absorption spectrum (IR, vmax cm$^{-1}$, KBr):
  2792, 1502, 1486, 1230, 1036, 932, 712
Ultraviolet absorption spectrum (vmax nm (log $\lambda$), EtOH]:
219 (4.28), 262 (4.05),
330 (4.32), 2.18 (6H,s),
5.99 (4H, s),
6.87 (2H, d, J=8.0 Hz),
7.14 (2H, dd, J=2.0, 8.0 Hz),
7.16 (2H, br s)
Mass spectrum (EI–MS) m/z (%):
336 (M+, 100), 187 (22), 2168 (20)
High resolution mass spectrum
$C_{20}H_{16}O_5$:
Calculated value: 336.0992
Found value: 336.0987

EXAMPLE 7

3,4-dimethyl-2,5-bis(3,4-ethylenedioxyphenyl)furan as compound 7 shown in Table 2 was produced in the following manner:

12.2 g of 3,4-dimethyl-2,5-bis(3-dihydroxy-diphenyl) furan obtained from compound 1) in the same manner as in Example 6, was dissolved in 70 ml of dimethylformamide and then the inner air of a reaction vessel was replaced with argon gas three times. Thereafter, 12.60 g of anhydrous potassium carbonate was added to the reaction solution and the inner air of the reaction vessel was replaced again with argon gas three times. Afterward, to the reaction solution, 3.94 ml of dibromoethane was added, and the mixture was stirred for 6 hours at 60° C. After the completion of the reaction was confirmed by TLC, the reaction solution was diluted with ethyl acetate and washed with 2N hydrochloric acid, water, saturated sodium hydrogen carbonate and brine, in this order. Thereafter, the reaction solution was dried over anhydrous magnesium sulfate and concentrated, to dryness, affording 3.94 g of residue. The residue obtained was subjected to silica gel column chromatography [column size: (4.5 cm (diameter)×40 cm, Kiesel gel 60, 70–230 mesh, 300 g, hexane-ethyl acetate (8:1, 6:1), 15 ml/fraction]. Fractions 31 to 53 were combined and concentrated, affording 1,258 g of compound (7).

Physicochemical properties of compound (7) are as follows:

Description: White powder

Infrared absorption spectrum (IR, vmax cm$^{-1}$, KBr): 2976, 1583, 1454, 1280, 1068, 926, 712

Ultraviolet absorption spectrum ($\lambda$ max nm (log $\epsilon$), EtOH]:

327 (4.32), 242 (4.11), 2.21 (4.27)

Proton nuclear magnetic resonance spectrum ($\delta$ ppm in CDCl$_3$):

2.18 (6H, s), 4.27 (8H,s), 6.89 (2H, d, J=8.0 Hz), 7.16 (2H, dd, J=2.0, 8.0 Hz), 7.19 (2H, d, J=2.0 Hz),

Mass spectrum (EI–MS) m/z (%):
364 (M+, 100), 182 (12)

High resolution mass spectrum $C_{22}H_{20}O_5$:

Calculatedvalue: 364.1310

Found value: 364.1306

EXAMPLE 8

2,5-bis(3'-hydroxyl-4'-methoxyphenl)-3,4-dimethylfuran as compound (8) shown in Table 2 was obtained in the following manner:

At first, 100 g of starting 3-hydroxy-4-methoxy-benzaldehyde was dissolved in 700 ml of dimethylformamide. To this solution, 100 g of ,anhydrous potassium carbonate and 90 ml of benzyl bromide were added, and the mixture was stirred for 6 hours at 90° C. After the completion of the reaction was confirmed by the disappearance of the starting material by means of TLC, the resultant solution was diluted with ethyl acetate, followed by washing twice with 1 liter of water. The ethyl acetate layer obtained was washed with 2N hydrochloric acid and a saturated aqueous sodium hydrogen carbonate solution in this order, dried with anhydrous magnesium sulfate and concentrated. Since dimethylformamide remained in the residue, the residue did not solidified. Thus, 158.65 g of a product in a form of a light yellow oily material was obtained. To this residue, 150 ml of methanol was added and allowed to stand still in a low temperature room, overnight. The crystal generated was collected by filtration under reduced pressure, affording 123.51 g of 3-benzyloxy-4methoxybenzaldehyde (78% yield).

To a three-neck flask, 187 ml of a 30M ethyl magnesium bromide ether solution was poured and stirred for 5 minutes under ice cooling. To this solution, 400 ml of a toluene solution in which 123.51 g of 3-benzyloxy-4-methoxybenzaldehyde was dissolved, and the mixture was added dropwise from a dropping funnel over 20 minutes. The reaction solution was stirred for additional 2 hours under ice cooling. After the completion of the reaction, the reaction solution was diluted by adding 300 ml of ethyl acetate. Further, pulverized sodium sulfate decahydrates was added to the reaction solution, which was stirred for 2 hours until a precipitate becomes smoothly. After allowed to stand still for 3 hours, the reaction solution was filtered under reduced pressure, separating into a supernatant and a precipitate. The supernatant was concentrated to dryness, affording 140.57 g of 1-(3'-benzyloxy-4'-methoxyphenyl) propanol.

On the other hand, while cooling i! an ice bath, 41 ml of concentrated sulfuric acid was added to 72 ml of water. To this, further, 48 g of chromium oxide (–) was added, stirred and a total volume was adjusted to 350 ml by adding water, thereby preparing the Jones reagent.

140.57 g of 1-(3'-benzyloxy-4'-methoxyphenyl) propanol previously-obtained was dissolved in 830 ml of acetone. To this solution, 350 ml of the Jones reagent was added little by little over 1 hour under ice-cooling (at 1° to 10° C.) and the mixture was stirred for another one hour. After the completion of the reaction, 500 ml of isopropyl alcohol was added to the reaction solution and the mixture was allowed to stand still until the color of the solution turned to green. Thereafter, the reaction solution was extracted three times with dichloromethane. The dichloromethane layer obtained was washed with water, a saturated aqueous sodium hydrogen carbonate solution and brine in this order and dried over anhydrous magnesium sulfate and further concentrated. The residue obtained was, crystallized from dichloromethane-methanol, affording 100.01 g of 3-benzyloxy-4-methoxy-propiophenone (73).

100 g of 3-benzyloxy-4-methoxypropiophenone obtained was dissolved in 1.0 liter of tetrahydrofuran. To this solution, 100 g of sodium bis(trimethylsilyl) amide was added, the resultant mixture was heated to 80° C., and stirred for 30 minutes. Subsequently, Iodide was dissolved in 0.5 liter of tetrahydrofuran solution. This tetrahydrofuran solution was added dropwise to the reaction solution at one time from a dropping funnel, and the resultant mixture was continuously stirred for additional 30 minutes.

After allowed to cool, the reaction solution was ice-cooled for additional 30 minutes. To this reaction solution, 1 liter of saturated. ammonium chloride was added, and the mixture was stirred for another one hour. The reaction solution was extracted with 1 liter of ethyl acetate. The ethyl acetate layer obtained was washed with a saturated aqueous sodium thiosulfate solution, water, 2N hydrochloric acid, a saturated aqueous sodium hydrogen carbonate solution and brine in this order. Subsequently, the ethyl acetate layer was dried over anhydrous magnesium sulfated concentrated to dryness. The residue obtained was subjected to silica gel column chromatography [Kiesel gel 60, 70–230 mesh (1 kg), hexane: ethyl acetate (5:1), fractions 1–20 (3:1), fractions 21–40, each fraction: 1 liter]. Fractions 26 to 40 were concentrated to dryness, affording 40.84 g of (±–2,3-bis(3-benzyloxy-4-methoxy benzoyl) butane (41% yield)

40.84 g of (±)-2,3-bis(3-benzyloxy-4-methoxybenzoyl) butane obtained was dissolved in 740 ml of chloroform. To this solution, 740 ml of methanol solution containing 8.7 ml of acetyl chloride was added, and the mixture was stirred for 2 hours at 70° C. Subsequently, the reaction solution was concentrated and the residue obtained was crystallized from dichloromethane-methanol, affording 32.16 g of 2,5-bis (3'-benzyloxy-4'-methoxyphnyl)furan (82% yield).

Physicochemical properties of the product are as follows:
Infrared absorption spectrum (IR, vmax cm$^{-1}$, KBr):
1600, 1584, 1512, 1254, 1218, 1014

Proton nuclear magnetic resonance spectrum (δ ppm in CDCl₃):

2.05 (6H, s), 3.92 (6H, s),
5.21 (4H, brs),
6.95 (2H, d, J=8.8 Hz),
7.18–7.50 (14H, m), Mass spectrum (EI–MS) m/z (%):
520 (M+, 77), 401 (58), 295 (22), 91 (100)

High resolution mass spectrum $C_{34}H_{22}O_5$:

Calculated value: 520.2250

Found value: 520.2262

32.16 g of 2,5-bis(3'-benzyloxy-4'-methoxyphenyl)furan obtained in the previous step, was dissolved in 1700 ml of tetrahydrofuran and 290 ml of methanol was further added thereto. To this solution, 430 mg of PdCl₂ was added, and the mixture was stirred for 5 hours at room temperature under hydrogen gas-flow. After the completion of the reaction, the filtrate obtained by filtration using a celite was concentrated. The residue exhibiting a deep-green color was dissolved in 100 ml of dichloromethane. To this solution, 500 ml of methanol was added and the generated precipitate was collected by filtration, affording 21.88 g of yellow-white precipitate. The precipitate was subjected to silica gel column chromatography [Kiesel gel 60, 70–230 mesh (300 g), hexane-ethyl acetate (3:1), 100 ml/fraction]. Fractions 9 to 33 obtained were combined and concentrated. The residue was crystallized from hexane-ethyl acetate, affording 14.8393 g of compound (8).

On the other hand, 3.54 g of the fraction obtained by subjecting the residue to silica gel column chromatography and eluting with methanol was further subjected to silica gel column chromatography [made by Kusano Kagaku Sha, CIG column., column size; 50 mm (diameter)×300 mm, hexane-ethyl acetate (3:1), 15 ml/fraction]. Fractions 51 to 150 obtained were combined and concentrated and the residue was crystallized from hexane-ethyl acetate, thereby recovering 3.3729 g of compound (8). By combining compound (8) obtained in this manner previously obtained one, compound (8) was finally obtained in an amount of 18.21 g (87% yield).

Physicochemical properties of compound (8) are as follows:

Description: colorless needle crystal

Melting point: 130°–131° C.

Infrared absorption spectrum (IR, νmax cm⁻¹, KBr):
3436, 1578, 1510, 1290, 1260, 1014, 868

Proton nuclear magnetic resonance spectrum (δ ppm in CDCl₃):

2.19 (6H, s), 3.91 (6H, s), 5.64 (2H, brs),
6.90 (2H, d, J=8.5 Hz),
7.20 (2H, dd, J=2.0, 8.5 Hz),
7.28 (2H, d, J=2.0 Hz), Carbon nuclear magnetic resonance Spectrum (δ ppm in CDCl₃):

9.8, 56.1, 110.8, 112.0, 117.7, 118.0, 125.9, 145.5, 145.6, 146.7

Mass spectrum (EI–MS) m/z (%):
340 (M+, 100), 325 (47),: 297 (11), 170 (22)

High resolution mass spectrum $C_{20}H_{20}O_5$:

Calculated value: 340.1311

Found value: 340.1321

EXAMPLE 9

2,4-bis(4-hydroxy-3-methoxyphenyl)-3,5-dimethylfuran as compound (9) shown in Table 3 was obtained in the following manner:

100 g of 4-hydroxy-3-methoxybenzaldehyde was dissolved in 700 ml of dimethylformamide, further 100 g of anhydrous potassium carbonate and 90 ml of benzyl bromide were added thereto, and the mixture was stirred for 1.5 hours at 80° C. After the completion of the reaction, the reaction solution was poured into 1 liter of water and extracted with 300 ml of ethyl acetate three times. The ethyl acetate layer was washed with water twice and dried over anhydrous magnesium sulfate and then concentrated. The residue obtained was crystallized from methanol, affording 142.95 g of 4-benzyloxy-3-methoxybenzaldehyde (89% yield).

Subsequently, to a flask, 130 ml of 3.0M ethyl magnesium bromide ether solution was placed and stirred for 5 minutes under ice-cooling. To this, 300 ml of toluene solution in which 85.53 g of 4-benzyloxy-3-methoxybenzaldehyde was dissolved, was added dropwise from a dropping funnel over 3 to 40 minutes and stirred for additional 20 minutes under ice-cooling. After the completion of the reaction, 200 ml of water was added little by little to the resultant mixture, and an organic layer and a water layer were separated. The water layer was extracted with toluene three times. The toluene layer obtained was combined witch the organic layer previously obtained. The organic layer thus obtained was washed with water, saturated sodium hydrogen carbonate and brine, in this order, dried over anhydrous magnesium sulfate, and concentrated. The residue was crystallized from methanol, affording 93.02 g of 4-benzyloxy-3-methoxypropiophenol (100% yield).

On the other hand, while cooling in an ice bath, 27 ml of concentrated sulfuric acid was added to 48 ml of water and 32 g of anhydrous chromium oxide was added thereto, and a total amount was adjusted to 235 ml by adding water, affording Jones reagent.

93.02 g of 4-benzyloxy-3-methoxypropiophenol obtained in the previous step was dissolved in 550 ml of acetone and 230 ml of Jones reagent was added dropwise thereto little by little under ice-cooling at a temperature between 0° to 10° C. while stirring for one hour. After the completion of the reaction, 100 ml of isopropyl alcohol was added to the reaction solution until the color turned to green, and allowed to stand still. The reaction solution was extracted with dichloromethane three times. The dichloromethan layer obtained was washed with water, a saturated aqueous sodium hydrogen carbonate solution and brine, in this order, dried over anhydrous magnesium sulfate and concentrated. The residue obtained was crystallized from dichloromethane/isopropyl ether, affording 53.22 g of 4-benzyloxy-3-methoxy-propiophenone (58% yield).

A tetrahydrofuran solution of diisopropylamine was placed in a three-neck flask and the inner air was replaced with argon gas. After the resultant solution was cooled to −70° C.° C., an n-butyllithium/hexane solution was added thereto and the resultant solution was stirred for 10 minutes at −70° C. To this solution, a tetrahydrofuran solution of 4-benzyloxy-3-methoxypropiophenone was added, and the resultant mixture was stirred for 30 minutes at −70° C. Further, a tetrahydrofuran solution of N-chlorosuccinimide was added thereto and stirred for 10 minutes at −70° C. After the temperature of the reaction solution was raised to room temperature and continuously stirred for additional 1.5 hours. As a result, the reaction solution was gradually stained with an orange color. Thereafter, a saturated ammonium chloride solution was added to the resultant solution and the resultant mixture was stirred for 30 minutes. After the solution was diluted by adding ethyl acetate, the ethyl acetate layer was washed with water, 2N hydrochloric acid, a saturated aqueous sodium hydrogen carbonate solution and brine, in this order. After the ethyl acetate layer was dried over anhydrous magnesium sulfate, the solution was concentrated to dryness, affording 38.48 g of residue. The residue was subjected to silica gel column [Kiesel gel 60, 70–230 mesh (380 g), hexane-ethyl acetate (5:1), 500 ml/fraction]. Fractions 17 to 26 were combined, concentrated to dryness, affording 7.1 g of 1,3-(4-benzyloxy-3-methoxyphenyl-3,4-epoxy-2- methyl-1-one-penthane.

1,3-(4-benzyloxy-3-methoxyphenyl-3,4-epoxy-2-methyl-1-one-penthane obtained was dissolved in chloroform. To this solution, a methanol solution of acetyl chloride was added, and the mixture was stirred for 2 hours at 90° C. The reaction solution was concentrated and the residue was subjected to a silica gel column [Kiesel gel 60, 70–230 mesh (140 g), hexane-ethyl acetate (5:1), 1 liter/fraction], Fractions 2 to 6 were combined and concentrated to dryness, affording 6 g of 3,5-dimethoxy-2,4-bis(3-benzyloxy-4-methoxyphenyl)furan.

6 g of 3,5-dimethoxy-2,4-bis(3-benzyloxy-4-methoxyphenyl)furan obtained was dissolved in 300 ml of tetrahydrofuran and further 50 ml of methanol was added thereto. To this solution, 80 ml of $PdCl_2$ was added, and the mixture was stirred for 3 hours at room temperature under hydrogen gas-flow. After the completion of the reaction, the solution was filtered through celite. The filtrate was concentrated, affording 4.44 g of residue. The residue was subjected to a silica gel column [CIG column chromatography (size: 22 mm (diameter)×300 mm , hexane-ethyl acetate (4:1), 15 ml/fraction]. Fractions 85 to 123 were combined, and concentrated, affording 2.29 g of compound (9).

Physicochemical properties of compound (9) are as follows:

Description: light brown powder

Infrared absorption spectrum (IR, vmax $cm^{-1}$, KBr):
3368, 1630, 1600, 1514, 1390

Ultraviolet absorption spectrum (vmax nm (log ε), EtOH]:
210 (4.48), 233 (4.19), 288 (4.29)

Proton nuclear magnetic resonance spectrum (δ ppm in $CDCl_3$):

2.15 (3H, s), 2.34 (3H, s),. 3.91 (6H, s), 3.96 (3H, s), 5.64 (1H, s), 5.65 (1H, s), 6.78 (1H, d, J=2.0 Hz), 6.79 (1H, dd, J=2.0, 8.5 Hz), 6.96 (1H, d, J=8.0 Hz), 6.98 (1H, d, J=8.5 Hz), 7.12 (1H, dd, J=2.0, 8.0 Hz), 7.17 (1H, d, J=2.0 Hz),

Carbon nuclear magnetic resonance Spectrum (δ ppm in $CDCl_3$):

10 10.7, 12.4, 56.0, 108.3, 112.3, 114.5, 115.0, 118.9, 122.8, 124.6

124.7, 125.7, 144.5, 146.4, 146.6, 146.9

Mass spectrum (EI–MS) m/z (%):
340 (M+)

EXAMPLE 10

2,5-bis(4'-hydroxy-3'-methoxyphenyl)-3,4-diisobutylfuran as compound (10) shown in Table 2 was obtained in the following manner:

To 10 g of magnesium, 5 m2of tetrahydrofuran was added and further 2 drops of 1,2-dibromoethane were added thereto. After the reaction mixture turned to slightly opaque, a mixed solution of 30 ml of 1-bromo-3-methylbutane and 30 ml of tetrahydrofuran was begun to add dropwise. When the reaction mixture generated heat, 40 ml of tetrahydrofuran was added at one time. Likewise, while the temperature of the reaction mixture was being maintained so as to calmly generate heat, the mixed solution was continued to drop. After the completion of the dropping, the reaction mixture was stirred for 2 hours at room temperature.

50 g of 4-benzyloxy-3-methoxybenzadehyde described in the aforementioned *ORGANIC PREPARATIONS PROCEDURES INTERNATIONAL* was dissolved in 150 ml of toluene. While cooling an ice bath, this solution was added dropwise into the previous reaction mixture. After the completion of the dropping, the reaction mixture was stirred for 30 minutes while cooling in an ice bath. Subsequently, to the reaction mixture, excessive sodium sulfate decahydrates was added. After the reaction mixture was stirred overnight, the precipitate generated was filtered. The resultant filtrate was concentrated, affording 64.5 g of 1-(4'benzyloxy-3'-methoxyphenyl)-methylpentanol (97.8% yield).

Separately, to 27 ml of water, 15 ml of concentrated sulfuric acid was added while cooling in an ice bath. To this solution, 18 g of chromium oxide (−) was added, and the mixture was stirred and then the total volume is adjusted to 130 ml by adding water, thereby preparing Jones reagent.

The previously obtained 63.0 g of 1-(4'benzyloxy-3'-methoxyphenyl)-4-methylpentanol was dissolved in 310 ml of acetone. To this mixture, Jones reagent was added dropwise at 0° to 10° C. while cooling in an ice bath. After the completion of dropping, 50 ml of isopropyl alcohol was added to the solution and the resultant mixture was stirred at room temperature until the solution turned to green. Subsequently, the reaction solution was extracted with 400 ml of dichloromethane three times. The extraction solution obtained was washed with 300 ml of water, 300 ml of saturated aqueous sodium hydrogen carbonate solution, and 300 ml of brine, in this order. After dried over anhydrous magnesium sulfate, the solution was concentrated under reduced pressure, affording a brown crystal. The crystal were recrystallized from ether-hexane, affording 51.6 g of 4'-benzyloxy-3'-methoxy-4-methylvalerophenone (82.6% yield).

40 g of 4'-benzyloxy-3'-methoxy-4-methylvalerophenone obtained was dissolved in 600 ml of tetrahydrofuran. To this solution, 40.8 g of sodium bis(trimethylsilyl) amide was added,the mixture was heated under reflux for 30 minutes. Subsequently, 25.6 g of iodine was dissolved in 200 ml of tetrahydrofuran. This tetrahydrofuran solution was added to the reaction solution at one time and further the mixture was heated under reflux for 30 minutes. After the reaction solution was allowed to stand in cool, 400 ml of saturated aqueous ammonium chloride solution was added, and the mixture was stirred. Thereafter, to the reaction solution, 500 ml of ethyl acetate was added and the ethyl acetate layer was washed with 600 ml of saturated aqueous sodium thiosulfate solution, 600 ml of water, 600 ml of 2N hydrochloric acid, 600 ml of saturated aqueous sodium hydrogen carbonate solution and 600 ml of brine, in this order. After the ethyl acetate layer washed was dried over anhydrous magnesium sulfate, it was concentrated under reduced pressure. The residue was separated by silica gel column chromatography (dichloromethane) and a blown solid material was obtained. The solid material was dissolved in 650 ml of chloroform. To this, a mixed solution of 7.6 ml of acetyl chloride and 1260 ml of methanol was added. After the mixture was heated under reflux for 2 hours, the reaction mixture was concentrated under reduced pressure. The residue obtained was separated by silica gel column chromatography (dichloromethan - hexane 2:3), affording blown crystals. The crystals were recrystallized from ethanol, and 22.7 g of 2,5-bis(4'-benzyloxy-3'-methoxyphenyl-3,4-diisobutylfuran was obtained (58.7% yield).

Physicochemical properties of the product are as follows:
Description: white needle crystals
Melting point: 113.1° C.
Infrared absorption spectrum (IR, vmax $cm^{-1}$, KBr):
  2952, 1512, 1454, 1274, 1252, 1218 1144, 1026, 790
Proton nuclear magnetic resonance spectrum ($\delta$ ppm in $CDCl_3$):
  0.93 (12H, d, J=6.6 Hz),
  1.80–1.97 (2H, m),
  2.52 (4H, t, J=7.3 Hz), 3.95 (6H, s) 5.19 (4H, s),
  6.90–6.94 (2H, m) 7.16–7.48 (14H, m)
Mass spectrum (EI–MS) m/z (%):
  604 (M+)
Elemental analysis
Theoretical value C: 79.44, H: 7.33
Found value C: 79.63, H: 7.25

9.0 g of 2,5-bis(4'-benzyloxy-3'-methoxyphenyl)-3,4-diisobutylfuran obtained as above Was dissolved in 100 ml of tetrahydrofuran and further 20 ml of methanol was added thereto. To this solution, 100 mg of palladium chloride was added as a catalyst and stirred for 3 hours under hydrogen gas flow at room temperature. Palladium chloride was filtered off by filtration using a celite and the filtrate was concentrated under reduced pressure, affording white crystals. The crystals were recrystallized from methanol-water, affording 5.8 g of compound (10) (92.0% yield).

Physicochemical properties of compound (10) are as follows:

Description: white plate crystals
Melting point: 113.2–114.0 ° C.
Infrared absorption spectrum (IR, vmax , $cm^{-1}$, KBr):
  3552, 1510, 1272, 1250, 1220, 1198, 788
Proton nuclear magnetic resonance Spectrum ($\delta$ ppm in $CDCl_3$):
  0.93 (12H, d, J=6.8 Hz),
  1.81–1.97 (2H, m),
  2.52 (4H, t, J=7.3 Hz),
  3.94 (6H, s), 5.63 (2H, s),
  6.93–6.98 (2H, m)
  7.17–7.24 (4H, m)
Mass spectrum (EI–MS) m/z (%):
  424 (M+)
High resolution mass spectrum
Theoretical value: 424.22497
Found value C: 424.22536
Elemental analysis
Theoretical value C: 73.56, H: 7.60
Found value C: 73.33, H: 7.61

EXAMPLE 11

2,5-bis(4'-hydroxy-3',5'-dimethoxyphenyl)-3,4-dimethylfuran as compound (11) shown in Table 2 was obtained in the following manner:

At first, 120 ml of ethyl magnesium bromide was stirred for 5 minutes while cooling in an ice bath. To this solution, a solution of 50 g of 4-benzyloxy-3,5-dimethoxybenzaldehyde synthesized in accordance with the method described in *Journal of Natural Products*, Vol. 154, NO1(1991), p110–118 in 150 ml of tetrahydrofuran in was added dropwise over 30 minutes. After the completion of the dropping, the reaction solution was stirred for one hour while cooling in an ice bath. Subsequently, excessive sodium sulfate decahydrates was added to the reaction solution and stirred overnight. The precipitate generated was filtered off, the filtrate was concentrated under reduced pressure. Oily material generated was dissolved in 250 ml of acetone to make a solution.

Separately, to 24 ml of water, 13.5 ml of concentrated sulfuric acid was added while cooling in an ice bath, further 16 g of chromium oxide (–) was added thereto and the resultant solution was stirred. The total volume is adjusted to 115 ml by adding water, thereby preparing Jones reagent.

To the previously obtained solution, Jones reagent was added dropwise at 0° to 10° C. After the completion of dropping, 50 ml of isopropyl alcohol was added to the solution and the resultant mixture was stirred. When the solution turned to green, stirring was stopped, and the reaction solution was extracted with 300 m of dichloromethane three times. The extract obtained was washed with 300 ml of water, 300 ml of saturated aqueous sodium hydrogen carbonate, and 300 ml of brine, in this order. After dried over anhydrous magnesium sulfate, the extraction solution washed was concentrated under reduced pressure. The obtained blown crystals were purified by silica gel column chromatography [ethyl acetate-hexane (1:9)], affording white crystals. The crystals were recrystallized from ether-hexane, affording 30.1 g of 4'-benzyloxy-3',5'-dimethoxypropiophenone (55.1% yield).

30 g of 4'-benzyloxy-3',5'-dimethoxypropiophenone obtained was dissolved in 450 ml of tetrahydrofuran. To this solution, 28 g of sodium bis(trimethylsilyl) amide was added, the resultant mixture was heated under reflux for 30 minutes. Subsequently, 150 ml of tetrahydrofuran solution in which 19 g of iodine was dissolved, was added to this reaction solution at one time and further the resultant mixture was heated under reflux for 30 minutes. After the reaction solution was allowed to stand in cool, 300 ml of saturated aqueous ammonium chloride solution was added and the resultant mixture was further stirred. To the reaction solution, 500 ml of ethyl acetate was added and the ethyl acetate layer was washed with 450 ml of saturated aqueous sodium thiosulfate solution, 450 ml of water, 450 ml of 2N hydrochloric acid, 450 ml of saturated aqueous sodium hydrogen carbonate solution and 450 ml of brine, in this order. After the ethyl acetate layer Washed was dried over anhydrous magnesium sulfate, it was concentrated under reduced pressure. The residue obtained was dissolved to 500 ml of chloroform and a mixed solution of 5.9 ml of ethyl chloride and 970 ml of methanol was added thereto. The mixed solution was heated under reflux for 1.5 hours, the reaction mixture was concentrated under reduced pressure. The residue obtained was purified by silica gel column chromatography [dichloromethane-hexane (3:2)], and a pink solid material was obtained. The Solid material was recrystallized from ethyl acetate, affording 12.3 g of 2,5-bis(4'-benzyloxy-3',5'dimethoxyphenyl)-3,4-dimethylfuran (42.2% yield).

Physicochemical properties of the product are as follows:
Description: white needle crystal
Melting point: 144.5°–146.0° C.
Infrared absorption spectrum (IR, vmax cm$^{-1}$, KBr):
1590, 1502, 1464, 1262, 1244, 1122
Proton nuclear magnetic resonance spectrum (δ ppm in CDCl$_3$):
2.24 (6H, s), 3.89 (12H, s),
5.05 (4H, s), 6.88 (4H, s),
7.26–7.54 (10H, m)
Mass spectrum (EI–MS) m/z (%):
580 (M+)
Elemental analysis
Theoretical value C: 74.16, H: 6.25
Found value C: 74 16, H: 6 34

8.7 g of 2,5-bis(4'-benzyloxy- 3'5'-dimethoxyphenyl–3,4-diisobutylfuran obtained as above was dissolved in 100 ml of tetrahydrofuran and further 20 ml of methanol was added thereto. To this solution, 100 mg of palladium chloride was added as a catalyst and the resultant mixture was stirred for 2 hours under hydrogen gas flow at room temperature. Palladium chloride was then filtered off by celite filtration and the filtrate was concentrated under reduced pressure, affording white crystals. The crystals were recrystallized from dichloromethane-hexane, affording 5.7 g of compound (11) (94.2% yield).

Physicochemical properties of compound (11) are as follows:
Description: blue needle crystal
Melting point: 160.5–161.7° C.
Infrared absorption spectrum (IR, vmax cm$^{-1}$, KBr):
1680, 1512, 1462, 1350, 1266, 1210, 1114
Proton nuclear magnetic resonance Spectrum (δ ppm in CDCl$_3$):
2.22 (6H, s), 3.95 (12H, s), 5.58 (2H, s),
6.88 (4H, s)
Mass spectrum (EI–MS) m/z (%):
400 (M+)
High resolution mass spectrum
Theoretical value: 400.15.220
Found value: 400.15289

EXAMPLE 12

Diethyl 2,5-bis(4'-hydroxy-3'-methoxyphenyl)furan-3,4-dicarboxylate as compound (12) shown in Table 2 was obtained in the following manner:

654 mg of diethyl 2,5-bis(4'-benzyloxy-3'-methoxybenzoyl) butane-1,4-dionate synthesized in accordance with the method described in *J. Org. Chem.*, Vol. 37, No. 26 1972, p4371–4376, was dissolved in 20 ml of chloroform and 0.19 g of p-toluenesulfonic acid monohydrate was added thereto. After this solution was heated under reflux for 24 hours, 80 ml of ethyl acetate was added, an ethyl acetate layer was Washed and with 30 ml of saturated aqueous sodium hydrogen carbonate solution. The ethyl acetate layer was dried over anhydrous magnesium sulfate, and concentrated under reduced pressure. The residue obtained was purified by silica gel column chromatography [ethyl acetate-hexane (1:4)] to afford yellow crystals. The crystals were recrystallized from ethanol, affording 215 mg of diethyl 2,5-bis(4'-benzyloxy-3'-methoxyphenyl)furan-3,4-dicarboxylate (33.8% yield).

Physicochemical properties of the product are as follows:
Description: white needle crystal
Melting point: 111.9°–112.4° C.
Infrared absorption spectrum (IR, vmax cm$^{-1}$, KBr):
1732, 1710, 1512, 1290, 1270, 1244, 1210, 1140, 1062, 1000
Proton nuclear magnetic resonance spectrum (δ ppm in CDCl$_3$):
1.32 (6H, t, J=7.1 Hz),
3.94 (6H, s),
4.31 (4H, q, J=7.1 Hz),
5.21 (4H, s),
6.91–6.95 (2H, m),
7.24–7.52 (14H, m)
Mass spectrum (EI–MS) m/z (%):
636 (M+)
Elemental analysis
Theoretical value C: 71.68, H: 5.70
Found value C: 71.48, H: 5.75

50.6 mg of diethyl 2,5-bis(4'-benzyloxy-3'-methoxyphenyl)furan-3,4-dicarboxylate was dissolved in 5 ml of ethyl acetate To the solution, 5 mg of 10% palladiumcarbon was added as a catalyst and the resultant mixture was stirred for 3 hours under hydrogen gas flow at room temperature. Palladium-carbon was filtered off by celite filtration, the filtrate was concentrated under reduced pressure, affording 40.2 mg of compound (12), quantitatively.

Physicochemical properties of compound (12) are as follows:
Description: colorless oil
Infrared absorption spectrum (IR, vmax cm$^{-1}$, KBr):
3540, 1720, 1510, 1464, 1376, 1328, 1268, 1230, 1170, 1098, 1058, 1032
Proton nuclear magnetic resonance Spectrum (δ ppm in CDCl$_3$):
1.33 (6H, t, J=7.1 Hz),
3.95 (6H, s),
4.32 (4H, q, J=7.1 Hz),
5.82 (2H, s),
6.95–7.00 (2H, m),
7.38–7.52 (4H, m)
Mass spectrum (EI–MS) m/z (%):
456(M+)
High resolution mass spectrum
Theoretical values 456.14203
Found value: 456.14136

EXAMPLE 13

2,5-bis(3'-hydroxy-4'-methoxyphenyl-3,4-diisobutylfuran as compound (13) shown in Table 2 was obtained in the following manner.

To 10 g of magnesium, 5 ml of tetrahydrofuran was added and 2 drops of 1,2-dibromoethane were added thereto. After the reaction solution turned to white opaque, a mixed solution of 3 ml of 1-bromo-3-methylbutane and 30 ml of tetrahydrofuran was begun to add dropwise. When the reaction mixture generated heat during the dropwise addition of the mixed solution, 40 ml of tetrahydrofuran was added at one time. Likewise, while the temperature of the reaction mixture was being maintained gently exothermic, the dropwise addition was continued. After the completion of the addition, the reaction mixture was stirred for 1 hour at room temperature.

50 g of 3-benzyloxy-4-methoxybenzaldehyde obtained in Example 8 was dissolved in 150 ml of toluene. This solution was added dropwise to the previous reaction solution over 20 minutes while, cooling in an ice bath. After the completion of the addition, the reaction solution was stirred for 20 minutes while cooling in an ice bath. To this reaction solution, excessive sodium sulfate decahydrates was added, and the resultant mixture was stirred overnight. The precipitate generated was filtered off and the filtrate was concentrated under reduced pressure and the oily material generated was dissolved in 310 ml of acetone.

To 27 ml of water, 15 ml of concentrated sulfuric acid was added while cooling in an ice bath. 18 g of chromium oxide (−) was added, and the mixture was stirred and the total volume is adjusted to 130 ml by adding water, thereby preparing Jones reagent.

The previously obtained solution, Jones reagent was added dropwise at 0° to 10° C. After the completion of the addition, 50 ml of isopropyl alcohol was added to the solution and the resultant mixture Was stirred. When the solution turned to green, the reaction solution was extracted with 300 ml of dichloromethane three times. The extract obtained was washed with 300 ml of water, 300 ml of saturated sodium hydrogen carbonate, and 300 ml of brine, in this order. After the extract washed was dried over anhydrous magnesium sulfate, it was concentrated under reduced pressure. The blown crystal obtained was recrystallized from hexane, affording 42.0 g of 3'-benzyloxy-4'-methoxy-4-methylvalerophenone (65.2% yield).

5 g of 3'-benzyloxy-4'-methoxy-4-methylvalerophenone obtained was dissolved in 75 ml of tetrahydrofuran. To this solution, 5.1 g of sodium bis(trimethylsilyl) amide was added, and the resultant mixture was stirred for 30 minutes at 80° C. A solution of 3.2 g of iodine in 25 ml of tetrahydrofuran was added to the reaction solution at one time and the mixture was stirred for additional 2 hours. After the reaction solution was allowed to stand in cool, 50 ml of saturated aqueous ammonium chloride solution was added, and the mixture was stirred. Thereafter, 800 ml of ethyl acetate was added to the reaction solution and the ethyl acetate layer was washed with 300 ml of saturated aqueous sodium thiosulfate solution, 300 ml of water, 300 ml of 2N hydrochloric acid, 300 ml of saturated aqueous sodium hydrogen carbonate solution and 300 ml of brine, in this order. After the ethyl acetate layer washed was dried over anhydrous magnesium sulfate, it was concentrated under reduced pressure. The residue obtained was purified by silica gel column chromatography [dichloromethane-hexane (1:2)] to obtain a blown solid material. The solid material was dissolved in 65 ml of chloroform. To this solution, a mixed solution of 0.7 ml of acetyl chloride and 120 ml of methanol was added. The resultant mixture was heated under reflux for 1.5 hours, and then concentrated under reduced pressure. The residue obtained was purified by silica gel column chromatography [dichloromethane-hexane (2:3)] to afford yellow crystals. The crystals were recrystallized from dichloromethane-hexane, affording 1.45 g of 2,5-bis(3'-benzyloxy-4'-methoxyphenyl)-3,4-diisobutylfuran (22.9% yield).

Physicochemical properties of the obtained product are as follows:

Description: white needle crystal

Melting point: 100.5°–101.4° C.

Infrared absorption spectrum (IR, νmax cm$^{-1}$, KBr):
2948, 2864, 1512, 1462, 1422, 1256, 1218, 1132, 1016

Proton nuclear magnetic resonance spectrum (δ ppm in CDCl$_3$):

0.87 (2H, d, J=6.6 Hz), 1.74–1.88 (2H, m), 2.43 (4H, d, J=7.3 Hz), 3.94 (6H, s), 5.19 (4H, s), 6.92–6.96 (2H, m)

7.21–7.64 (14H, m)

Mass spectrum (EI–MS) m/z (%):

604 (M+)

Elemental analysis

Theoretical value C: 79.44, H: 7.33

Found value C: 79.17, H: 7.32

604 mg of 2,5-bis(3'-benzyloxy-4'-methoxyphenyl)-3,4-diisobutylfuran obtained in this way was dissolved in 20 ml of tetrahydrofuran and 4 ml of methanol was added. To this solution, 10 mg of palladium chloride was added as a catalyst and the resultant mixture was stirred for 2 hours under hydrogen gas flow at room temperature. Palladium chloride was filtered off by celite filtration and the filtrate was concentrated under reduced pressure, affording white crystals. The crystals were recrystallized from ether-hexane, affording 340 mg of compound (13) (80.2% yield).

Physicochemical properties of compound (13) are as follows:

Description: white needle crystal

Melting point: 109.0°–109.5° C.

Infrared absorption spectrum (IR, νmax cm$^{-1}$, KBr):
2952, 1510, 1294, 1280, 1256, 1220, 1124

Proton nuclear magnetic resonance Spectrum (δ ppm in CDCl$_3$):

0.93 (12H, d, J=6.6 Hz), 1.76–1.97 (2H, m), 2.51 (4H, brs), 3.93 (6H, s), 5.62 (2H, brs), 6.87–6.91 (2H, s), 7.44 (4H, brs)

Mass spectrum (EI–MS) m/z (%):
424 (M+)

High resolution mass spectrum

Theoretical value: 424.22497

Found value: 424.22568

Elemental analysis

Theoretical value C: 73.56, H: 7.60

Found value C 73.39, H: 7.69

EXAMPLE 14

2,5-bis(4'-hydroxy-3'-methoxyphenyl)furan-3,4-dicarboxylic acid as compound (14) shown in Table 2 was obtained in the following manner:

542.2 mg of diethyl 2,5-bis(4'-hydroxy-3'-methoxyphenyl)furan-3,4-dicarboxylate as compound (12) obtained in Example 12 was dissolved in 25 ml of ethanol. To this solution, 2.4 ml of 10% sodium hydroxide was added and heated under reflux for 9 hours. After cooling, this solution was concentrated. The residue obtained was dissolved by adding 15 ml of water. To this solution, 5 ml of 2N hydrochloric acid Was added and the precipitate generated was filtered. This precipitate was washed with water and dried, affording a brown solid material. The solid material was recrystallized from methanol-water, affording 331.2 mg of compound (14) (69.6% yield).

Physicochemical properties of compound (14) are as follows:

Description: white powder

Infrared absorption spectrum (IR, νmax cm$^{-1}$, KBr):
1598, 1512, 1470, 1434, 1370, 1290, 1248, 1208, 1176, 1130

Proton nuclear magnetic resonance Spectrum (δ ppm in CDCl₃):
3.91 (6H, s), 6.86–6.90 (2H, m),
7.34–7.40 (2H, m) 7.55–7.56 (2H, m)
Mass spectrum (EI–MS) m/z (%):
400(M+)
High resolution mass spectrum
Theoretical value: 400.08124
Found value: 400.07943

EXAMPLE 15

Diethyl 2,5-bis(3'-hydroxy-4'-methoxyphenyl)furan-3,4-dicarboxylate as compound (15) shown in Table 2 was obtained in the following manner:

51 g of isovanillic acid was dissolved in 350 ml of N,N-dimethylformamide, further 80 ml of, benzyl chloride and 90 g of potassium carbonate were added thereto, and was the resultant mixture was stirred for 24 hours at 60° C. Thereafter, 30 ml of benzylchloride was added, and the resultant mixture was stirred for additional 15 hours at the same temperature. After cooling, 200 ml of triethylamine was added to the resultant solution and stirred for 30 minutes. The reaction mixture was poured into 150 ml of water and extracted with 300 ml of ethyl acetate three times. An organic layer was washed with 100 ml of water three times and 100 ml of 2N hydrochloric acid three times and 100 ml of water three times in this order. The organic layer was dried over anhydrous magnesium sulfate and then concentrated under reduced pressure. The residue was recrystallized from dichloromethane-ether, affording 98.3 g of 3-benzyloxy4-methoxybenzyl benzoate (93.0% yield). Physicochemical properties of the compound are as follows:

m.p. 75.7° C.

Infrared absorption spectrum (IR, νmax cm⁻¹, KBr):
1708, 1514, 1290, 1270, 1220, 1208, 1182, 1130, 1096, 1010, 760, 746

Proton nuclear magnetic resonance Spectrum (δ ppm in CDCl₃):
3.93 (6H, s), 5.17(2H, s)., 5.32 (2H, s),
6.88–6.92 (1H, m),
7.30–7.48 (10H, m),
7.62–7.75 (2H, m)
Mass spectrum (EI–MS) m/z (%):
348 (M+)
Elemental analysis
Theoretical value C: 75.84, H: 5.79
Found value C: 75.88, H: 5.89

80 g of benzyl 3-benzyloxy-4-methoxybenzyl benzoate obtained was dissolved in 460 ml of methanol with heating. 184 ml of 10% aqueous sodium hydroxide solution was added thereto and the resultant mixture was heated under reflux for 2 hours. After cooling, the reaction mixture was concentrated under reduced pressure, affording white crystals. The crystals were dissolved in 230 ml of water. To this solution, 2N hydrochloric acid was added to make this solution acidic. The precipitate generated was collected by filtration, dried and recrystallized from ethyl acetate, affording 55.1 g of 3-benzyloxy-4-methoxy benzoic acid (92.9% yield).

Physicochemical properties of the compound are as follows:

m.p. 177.5°–177.8° C.

Infrared absorption spectrum (IR, νmax cm⁻¹, KBr):
1666, 1596, 1584, 1512, 1442, 1296, 1274, 1230, 998

Proton nuclear magnetic resonance Spectrum (δ ppm in CDCl₃):
3.95 (6H, s), 5.19 (2H, s),
6.91–6.96 (1H, m),
7.31–7.49 (5H, m),
7.65–7.80 (2H, m)
Mass spectrum (EI–MS) m/z (%):
258 (M+)
Elemental analysis
Theoretical value C: 69.75, H: 5.46
Found value C: 69.81, H: 5.56

35 g of 3-benzyloxy-4-methoxy benzoic acid was dissolved in 75 ml of thionyl chloride and the resultant mixture was heated under reflux for 70 hours. After cooling, benzene was added to the reaction mixture, and the mixture was concentrated under reduced pressure. The crystals generated were dissolved in 200 ml of tetrahydrofuran (referred to as "Solution A"). On the other hand, 14 g of sodium hydride (60 i% oil) was washed with 30 ml of hexane three times. To this, 175 ml of ether was added in an argon atmosphere, affording a suspension. A mixture of 53 g of ethyl acetoacetate and 175 ml of ether were added to this suspension and the resultant mixture was heated under reflux for one hour. To the reaction mixture, Solution A was added and the resultant mixture was heated under reflux for 5 hours. After this reaction mixture was stirred additional overnight at room temperature, 2N hydrochloric acid was added to make the reaction mixture acidic. An organic layer was separated and a water layer was extracted with 100 ml of ether three times. These organic layers were combined and washed with 100 ml of brine three times and dried over anhydrous magnesium sulfate. After drying, the organic layer was concentrated under reduced pressure. The brown oily material generated was dissolved in 300 ml of 95% ethanol. To this ethanol solution, 60 g of sodium acetate was added and the resultant mixture was heated under reflux for 4 hours. After cooling, the reaction mixture was concentrated under reduced pressure. To the residue, 150 ml of water was added and the mixture was extracted with 100 ml of ethyl acetate three times. This extract was washed with 50 ml of saturated aqueous sodium hydrogen carbonate solution three times, with 50 ml of brine three times in this order and dried over anhydrous magnesium sulfate. Thereafter, the extract was concentrated under reduced pressure. The light yellow crystals generated were dissolved in 250 ml of acetonitrile. To this solution, 250 ml of water, 41.9 g of potassium persulfate and 3.69 g of copper (II) sulfate pentahydrate were further added and the resultant mixture was heated under reflux in an argon atmosphere. After cooling, 150 ml of dichloromethane was added to the reaction mixture and an organic layer was separated. The remaining water layer was extracted twice with 70 ml of dichloromethane and the organic extract was combined with the previous organic layer. This organic layer was dried over anhydrous magnesium sulfate and then concentrated under reduced pressure. The orange-colored crystals obtained were separated by silica gel column chromatography (dichloromethane), affording 14.2 g of white crystals. 1.3 g of crystals were dissolved in 40 ml of dichloromethane and p-toluenesulfonic acid monohydrate was added thereto and the resultant mixture was heated under reflux for 72 hours. After cooling, 80 ml of ethyl acetate was added to the reaction mixture. The resultant mixture was washed with 50 ml of saturated aqueous sodium hydrogen carbonate three times, dried over anhydrous magnesium sulfate, and concentrated under reduced pressure. The orange-colored oily material generated was separated by silica gel column chromatography (ethyl acetate-hexane=1:4), affording white crystals. The crystals were recrystallized from ethanol to obtain 78.1 mg of diethyl 2,5-bis(3'-benzyloxy-4'methoxyphenyl)furan-3,4-dicarboxylate as white needle crystals (21.5% yield).

Physicochemical properties of the compound are as follows:

m.p. 126.0°–126.5° C.

Infrared absorption spectrum (IR, vmax cm$^{-1}$, KBr):
 1720, 1512, 1338, 1258, 1242, 1218, 1142

Proton nuclear magnetic resonance Spectrum (δ ppm in CDCl$_3$):
 1.32 (6H, t, J=7.1 Hz), 3.94 (6H, s),
 4.28 (4H, q, J=7.1 Hz),
 5.19 (4H, s), 6.93–6.97 (2H, m),
 7.29–7.52 (14H, m)

Mass spectrum (EI–MS) m/z (%):
 636 (M+)

Elemental analysis
Theoretical value C: 71.68, H: 5.19
Found value C: 71.42, H: 5.88

837 mg of diethyl 2,5-bis(3'-benzyloxy-4'-methoxyphenyl)furan-3,4-dicarboxylate obtained was dissolved in 40 ml of ethyl acetate and 40 mg of 10% palladium-carbon was added thereto. The resultant mixture was stirred for 25 hours at room temperature in a hydrogen atmosphere. Thereafter, a catalyst was filtered off by celite filtration. The filtrate was concentrated under reduced pressure. The residue obtained was recrystallized from ethyl acetate-hexane, affording 587.5 mg of compound (15) as a white needle crystal (94.6% yield).

Physicochemical properties of the compound (15) are as follows:

m.p. 149.0°–149.9° C.

Infrared absorption spectrum (IR, vmax cm$^{-1}$, KBr):
 3380, 1732, 1720, 1512, 1274, 1242, 1218, 1094, 1064

Proton nuclear magnetic resonance spectrum (δ ppm in CDCl$_3$):
 1.34 (6H, t, J=7.1 Hz), 3.94 (6H, s),
 4.34 (4H, q, J=7.1 Hz),
 5.65 (2H, s), 6.88–6.92 (2H, m),
 7.40–7.46 (4H, m)

High resolution mass spectrum
Theoretical value m/z: 458.14203
Found value m/z: 458.14358

Elemental analysis
Theoretical value C: 63.15, H: 5.30
Found value C: 62.86, H: 5.37

EXAMPLE 16

Diethyl 2,5-bis(3'-hydroxy-4'-methoxyphenyl)furan-3,4-dicarboxylic acid as compound (16) shown in Table 2 was obtained in the following manner:

468 mg of diethyl 2,5-bis(3'-hydroxy-4'-methoxy-phenyl) furan-3,4-dicarboxylate (compound (15) obtained in Example 15 was dissolved in 25 ml o$_E$ ethanol. To this solution, 2.4 ml of 10% aqueous sodium hydroxide solution was added, and the resultant mixture was heated under reflux for 3 hours. After cooling, the reaction mixture was concentrated under reduced pressure. The residue was dissolved by adding 5 ml of water. To this solution, 2N hydrochloric acid was added to make this solution acidic. The precipitate generated was filtered, washed with water and dried. The brown powder obtained was recrystallized from methanol-water, affording 306.8 mg of a light blown powder as compound (16) in a yield of 74.7%. Physicochemical properties of compound (16) are as follows:

Infrared absorption spectrum (IR, vmax cm$^{-1}$, KBr):
 3256, 1708, 1616, 1508, 1442, 1258, 1222, 1138, 1098, 1022, 766

Proton nuclear magnetic resonance spectrum (δ ppm in CDCl$_3$):
 3.91 (6H, s), 4.34 (4H, q, J=7.1Hz),
 6.98–7.02 (2H, m), 7.37–7.42 (4H, m)

Mass spectrum
m/z: 400 (M+)

High resolution mass spectrum
Theoretical value m/z: 400.07943
Found value m/z: 400.08043

Using compounds (1) to (16) obtained above, the following experiments were carried out to confirm that the active ingredient of the present invention has a remarkable angiogenesis inhibition activity.

EXPERIMENT 1

Compound(s) as an active ingredient of the angiogenesis inhibitor of the present invention (hereinafter also simply referred to as "compound(s)") were evaluated with respect to an activity to cell migration with human HOME cells in which a wound healing had been made by a razor blade, and cell migration activity accelerated by TGF$_α$.

The HOME cells to be used in this experiment were isolated from human omental fatty tissues and cultured in a M-199 medium containing 10% fetal bovine serum (FBS) over 3 to 5 generations.

TGF$_α$ was obtained from Collaborative Research Inc., Bedford, Ma.

The HOME cells were cultured as a monolayer on a collagen-coated plastic dish (35 mm φ) to confluent. The thus obtained HOME cells were wounded with a razor blade and then washed twice with a phosphate buffer saline solution (PBS). Subsequently, the HOME cells were cultured at 37° C. for 24 hours in 1% human serum containing M-199 mediums, to which compounds (1), (2), (4), (5), (6), or (7) to (12) were individually added in an amount of 10 µl/ml. On the other hand, HOME cells were cultured at 37° C. for 24 hours in 1% human serum containing M-199 mediums to which TGF$_α$ was added in an amount of 10 ng/ml in addition to each of the aforementioned 12 compounds. Further, HOME cells were cultured in 1% human serum containing M-199 medium with neither active ingredient nor TGF$_α$ at 37° C for 24 hours to prepare a non-treatment group.

On the dish on which the HOME cells were cultured, the numbers of migrated HOME cells were counted, which migrated to the exposed portion of the Collagen-coated plastic dish. A cell-migration rate was calculated, regarding the cell migration numbers of the non-treatment group as 100%. The results are shown in Table 5.

TABLE 5

| COMPOUND<br>10 mg/ml added | Cell-migration rate (%) | |
|---|---|---|
| | TGF$_α$ Free | TGF$_α$ 10 mg/ml added |
| Non-treatment group | 100.0 | 100.0 |
| COMPOUND 1 | 13.9 | 24.0 |
| COMPOUND 2 | 69.0 | 68.2 |
| COMPOUND 3 | 52.7 | 73.1 |
| COMPOUND 4 | 50.2 | 60.4 |
| COMPOUND 5 | 89.0 | 75.8 |
| COMPOUND 6 | 45.2 | 59.9 |

TABLE 5-continued

| COMPOUND 10 mg/ml added | Cell-migration rate (%) | |
|---|---|---|
| | $TGF_\alpha$ Free | $TGF_\alpha$ 10 mg/ml added |
| COMPOUND 7 | 33.3 | 31.4 |
| COMPOUND 8 | 69.4 | 44.2 |
| COMPOUND 9 | 63.3 | 73.0 |
| COMPOUND 11 | 81.2 | 56.1 |
| COMPOUND 12 | 72.7 | 58.4 |

As is apparent from Table 5, the cell migration was inhibited approximately from 10 to 85% in the case where any of the compounds of the present invention was added to a $TGF_\alpha$-free medium in a final concentration of 10 µg/ml. In particular, in the case of compounds (1), (5), (6), and (8), approximately 50 to 86% of the cell migration was inhibited. In the case where any of the compounds of the present invention was added to a 10 µg/ml of $TGF_\alpha$ containing medium, the cell migration accelerated by $TGF_\alpha$ was inhibited to approximately 25 to 76%. In particular, the cell migration was inhibited to approximately 45 to 76% in the mediums containing compounds (1), (8) and (9).

As described in the foregoing, it was confirmed that the HOME cell migration and the HOME cell migration accelerated by $TGF_\alpha$ can be inhibited by the compounds of the present invention.

EXPERIMENT 2

The activity of the active ingredients to the tube formation of the HOME cells induced by $TGF_\alpha$ was determined.

At first, 8 volume of a type 1 collagen solution (manufactured by Nitta Gelatin .), 1 volume of 10×M-199 and 1 volume of a reconstituted buffer) [200 mM Hepes, 0.05N sodium hydroxide and 260 mM sodium hydrogen carbonate] were mixed under ice cooling. The mixture was placed on plastic dishes (30 mm diameter, manufactured by Corning.) and allowed to stand still at 37° C. to make gel, thereby preparing a type-1 collagen gel.

Subsequently, the HOME cells were suspended in 10% FBS containing M-199 medium and then dispersed on the type 1 collagen gel mentioned above and incubated at 37° C.

When the HOME cells were incubated to confluent, they were transferred to 1% human serum containing M-199 mediums to which compounds (1), (2) and (4) to (12) (a final concentration: 10 µg/ml) were individually added together with $TGF_\alpha$ (final concentration 10 ng/ml). These mediums were incubated for 3 days.

The HOME cells were also transferred to a 1% human serum containing M-199 medium with $TGF_\alpha$ alone to prepare a control group and transferred to a 1% human serum containing M-199 medium to prepare a non-treatment group. They were also incubated for 3 days.

Two days after the incubation started, the culture mediums were exchanged. At three days, photographic picture of each dish was taken by a video camera (R5000H, Fuji, Tokyo), using a phase-contrast microscope at 200 magnification of the object. 8 views were taken for each dishes. The total tube length per one view formed by the HOME cells was measured by using a Cosmozone IS image analyzer (manufactured by Nikon). The results are shown in Tables 6 and 7.

TABLE 6

| COMPOUND 10 µg/ml added | Total tube length/HPF ($10^3$ µm) |
|---|---|
| Non-treatment group | 0.616 |
| Control group | 2.045 |
| COMPOUND 2 | 1.115 |
| COMPOUND 4 | 2.127 |
| COMPOUND 6 | 1.240 |
| COMPOUND 7 | 1.195 |

TABLE 7

| COMPOUND 10 µg/ml added | Total length of lumen/HPF ($10^3$ µm) |
|---|---|
| Non-treatment group | 0.551 |
| Control group | 1.561 |
| COMPOUND 1 | 0.337 |
| COMPOUND 8 | 0.422 |
| COMPOUND 9 | 0.496 |
| COMPOUND 10 | 0.655 |
| COMPOUND 11 | 0.817 |
| COMPOUND 12 | 0.736 |

As is apparent from Tables 6 and 7, the tube formation induced by $TGF_\alpha$ was inhibited to 40 to 60% in the case where compounds (2), (6) and (7) were added in a final concentration of 10 µg/ml. The tube formation induced by $TGF_\alpha$ was inhibited to 50 to 80% in the case where compounds (1), (8), (9), (10), (11) and (12) were added in a final concentration of 10 µg/ml.

EXPERIMENT 3

In a co-culture of the HOME cells and human cancer cells, the activity of the compounds to the tube formation of the HOME cells induced by the human cancer cells was determined. This experiment was carried out in accordance with the co-culture method described in Morisaki, Saito, et al., "Co-culture test system of vascular endothelial cells and tunica media smooth muscle cells".

The HOME cells on the type-1 collagen gel prepared in Experiment 2 and human esophagus cancer cells (TE-1) were co-cultured to assemble a tube formation assay system. More specifically, using a plate (manufactured by Corning Co.,) having 6 holes (each hole size: 38×7 mm) in the outer vessel, 2 ml of 10% FBS containing M-199 medium was placed to each hole. The TE-1 cells were cultured in this medium. Thereafter, the medium was replaced with 2 ml of 1% FBS containing M-199 mediums which respectively contained compounds (1) and (8). Also, the medium was replaced with 1% FBS containing M-199 medium alone.

On the other hand, culture plates equipped with a Millipore filter at the inner vessel (size: 30×7 mm) bottom, were prepared. The type-1 collagen gel was placed in the inner vessel. On each of the type-1 collagen gel, 2 ml of the HOME cells suspension in the 10% FBS containing M-199 medium were planted. When the HOME cells reached a confluent condition, the serum component contained in the medium was changed from 10% FBS to 1% human serum. The inner vessel was then placed in the outer vessel in the predetermined conditions. In this assay system, a factor secreted from the cancer cells of the outer vessel reaches the inner vessel via the Millipore filter equipped at the bottom and makes the HOME cells to form tube like structure in the type-1 collagen gel.

In this experiment, the HOME cells were cultured without adding compounds and TE-1 cells to make a non treatment group. Furthermore, the HOME cells were co-cultured with TE-1 cells without adding the compounds of the present invention to make a control, group.

The total tube length in the HOME cells cultured was measured in the same manner as in Experiment 2. The results are shown in Table 8.

TABLE 8

| COMPOUND 10 µg/ml added | Total length of lumen/HPF ($10^3$ µm) |
|---|---|
| Non-treatment group | 0.348 |
| Control group | 1.551 |
| COMPOUND 1 | 0.250 |
| COMPOUND 8 | 0.277 |

AS is apparent from Table 8, compounds (1) and (8) inhibited the tube formation induced by a proliferation factor (mainly $TGF_\alpha$) secreted from the cancer cells to 40 to 60%, in a final concentration of 10 µg/ml.

From the results in the foregoing, It was confirmed that the compounds as an active ingredient of the angiogenesis inhibitor of the present invention have an endothelial cell migration inhibitory activity and a tube formation inhibitory activity, which are particularly found in the neovascularization process of small blood vessels such as capillaries and postcapillary venules.

EXPERIMENT 4

In-vivo anti-tumor activity of the compounds of the present invention was tested.

M-5076 (mouse ovarian reticulo sarcoma, mouse ovary cancer) was intraperitoneally (i.p.) inoculated in C57BL6 mouse, and maintained by ip passage. The obtained ascites tumor cells werediluted with PBS (−) to cellular number of $2\times10^7$ cells/ml. 50 µl of the dilute solution (cellular number: $1\times10^6$) was subcutaneously (s.c.) transplanted to the right dorsal part of C57BL6 mouse (6 week old, female). From 7 days after the tumor cell inocutation, a sample was administrated to the mouse. The sample was prepared by suspending compounds (1) and (8) in 2% Tween 80 PBS (−) solution. The suspension was subcutaneously injected to a mouse in a dose of 100 µl per mouse. Three dosages, i.e., 400 mg/kg, 200 mg/kg and 100 mg/kg were set for the injection.

Mitomycin C (MMC) and Fumagillin Were employed in positive controls. MMC was intravascularly injected 4 times every two day. Other test samples and Fumagillin were intravascularly injected 6 times in total in a rate of 3 times/week. The test was carried out using N=9 in controls and N=5 in other groups.

Twenty one days after the inocutation of the tumor cells (14 days after the next day of the initiation of the sample injection), a relative tumor proliferation rate were examined to determine the anti-tumor effect of the samples. The results are shown in Table 9 and FIG. 1.

TABLE 9

The relative tumor proliferation rate are indicated by the following equation.

| Sample name | Dosage (mg/kg) | Relative tumor proliferation rate(Trv/Crv(%)) | Significant difference P |
|---|---|---|---|
| Control | 0 | 100.0 | n.s. |
| Fumagillin | 30 | 41.7 | <0.05 |
| MMC | 3.2 | 7.9 | <0.05 |
| COMPOUND 1 | 400 | 51.3 | <0.05 |
| | 200 | 37.4 | <0.05 |
| | 100 | 37.1 | <0.01 |
| COMPOUND 2 | 400 | 37.4 | <0.01 |
| | 200 | 41.4 | <0.05 |
| | 100 | 59.4 | n.s. |

A significant difference test was performed by the Mann-Whitney U-Test.

$$\frac{\text{Tumor volume (14 days after the first day of the sample}}{\text{Tumor volume (The first day of the sample administration)}} \times 100$$

No death was observed at a determination day.

As is apparent from the result above, it is demonstrated that compounds (1) and (8) have a significant anti-tumor activity in vivo.

On the other hand, an acute toxicity of the active ingredients of the present invention was examined by orally administration the active ingredients, using ICR series mice. Even if the compound of the present invention was given in an amount of 1 g/kg, no death occurred.

From this result, it was confirmed that the compounds of the present invention have less toxicity and therefore they are high in safety.

Hereinafter, the specific formulations of the angiogenesis inhibitors of the present invention.

EXAMPLE 17

| (1) Cornstarch | 44 g |
|---|---|
| (2) Crystalline cellulose | 40 g |
| (3) Calcium carboxymethyl cellulose | 5 g |
| (4) Light anhydrous silicic acid | 0.5 g |
| (5) Magnesium stearate | 0.5 g |
| (6) Compound (6) | 10 g |
| Total | 100 g |

In accordance with the formulation above, components (1) to (6) were homogeneously mixed and compression-molded by a customarily-used tablet compressing machine to obtain tablets of 200 mg. Each tablet contains 20 mg of compound (6) obtained in Example 6. 3 to 10 tablets/day may be administrated to an adult several times a day.

EXAMPLE 18

| (1) Crystalline cellulose | 84.5 g |
|---|---|
| (2) Magnesium stearate | 0.5 g |
| (3) Calcium carboxymethyl cellulose | 5 g |
| (4) Compound (7) | 10 g |
| Total | 100 g |

In accordance with the formulation above, components (1), (4) and part of component (2) were homogeneously mixed and compression-molded by a customarily-used tablet compressing machine and then crushing. Subsequently, component (3) and the rest of component (2) were added to the crushed mixture, which was compress-molded once more by the customarily-used tablet compressing machine to obtain tablets of 200 mg. Each tablet contains 20 mg of compound (7) obtained in Example 7. 3 to 10 tablets/day may be administered to an adult several times a day.

EXAMPLE 19

| (1) Crystalline cellulose | 79.5 g |
| (2) Ethanol solution of 10% hydroxypropyl cellulose | 50 g |
| (3) Calcium carboxymethyl cellulose | 5 g |
| (4) Magnesium stearate | 0.5 g |
| (5) Compound (8) | 10 g |
| Total | 145 g |

In accordance with the formulation above, components (1), (2) and (5) were homogeneously kneaded in accordance with an ordinary method and granulated by a customarily-used extrusion granulation machine, followed by drying and crushing. Thereafter, components (3) and (4) were mixed therewith and compression-molded by a customarily-used tablet compressing machine to obtain tablets of 200 mg. Each tablet contains 20 mg of compound (8) obtained in Example 8. 3 to 10 tablets/day may be administered to an adult several times a day.

EXAMPLE 20

| (1) Cornstarch | 84 g |
| (2) Magnesium stearate | 0.5 g |
| (3) Calcium carboxymethyl cellulose | 5 g |
| (4) Light anhydrous silicic acid | 0.5 g |
| (5) Compound (9) | 10 g |
| Total | 100 g |

In accordance with the formulation above, components (1) to (5) were homogeneously mixed, compression-molded by a customarily-used compression molding machine, thereafter, crushed by a crusher and sieved to obtain granules. 1 g of the granular contains 100 mg of compound (9) obtained in Example 9. 0.6 to 2 g of the granules per day may be administered to an adult several times a day.

EXAMPLE 21

| (1) crystalline cellulose | 86.5 g |
| (2) 10% hydroxypropyl cellulose ethanol solution | 35 g |
| (3) Compound (10) | 10 g |
| Total | 131.5 g |

In accordance with the formulation above, components (1) to (3) were homogeneously kneaded, granulated by an extrusion granulation machine, dried and sieved to obtain granules. 1 g of the granular contains 100 mg of compound (10) obtained in Example 10. 0.6 to 2 g of the granules per day may be administered to an adult several times a day.

EXAMPLE 22

| (1) Cornstarch | 89.5 g |
| (2) Light anhydrous silicic acid | 0.5 g |
| (3) Compound (6) | 10 g |

In accordance with the formulation above, components (1) to (3) were homogeneously mixed. 200 g of the mixture was charged in No. 2 capsules to obtain capsules. Each capsule contains 20 mg of compound (6) obtained in Example 6. 3 to 10 capsules/day may be administered to an adult several times a day.

EXAMPLE 23

| (1) Distilled water for injection | 89.5 g |
| (2) Soybean oil | 5 g |
| (3) Soybean phospholipid | 2.5 g |
| (4) Glycerin | 2 g |
| (5) Compound (7) | 1 g |
| Total | 100 g |

In accordance with the formulation above, component (5) was dissolved in components (2) and (3). To this solution, solutions of component (1) and (2) were added and emulsify the mixture to obtain an injection agent.

EXAMPLE 24

| (1) Compound (8) | 0.05 g |
| (2) White Vaseline | 25 g |
| (3) Stearyl alcohol | 22 g |
| (4) White beeswax | 15 g |
| (5) Polyoxy ethylene (25) monostearate ester | 2.3 g |
| (6) Sorbitan monopalmitate | 2.7 g |
| (7) Paraoxy propyl benzoate | 0.05 g |
| (8) Paraoxy methyl benzoate | 0.05 g |
| (9) Purified water | 32.85 g |
| Total | 100 g |

In accordance with the formulation above, components (1) to (9) were homogeneously mixed, dissolved with heating to obtain an ointment.

We claim:

1. An angiogenesis inhibitor comprising, as an active ingredient, a mixture of

Compound I represented by general formula (I) below:

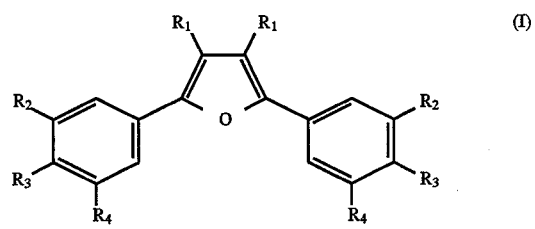

where $R_1$ is a lower alkyl group having 1 to 4 carbon atoms, an alkoxycarbonyl group having 1 to 4 carbon atoms in the alkoxy moiety or a carboxyl group; and $R_2$, $R_3$ and $R_4$ may be the same or different and each represents a hydrogen atom, a hydroxyl group, a methoxy group or an acetoxy group, wherein $R_2$ and $R_3$ may bind together to close a ring, as shown in general formula (II) below:

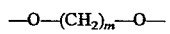 (II)

where m is an integer from 1 to 6;

Compound III represented by general formula (III) below:

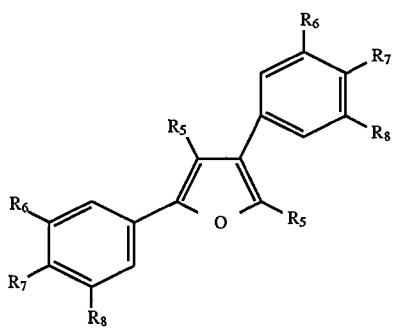 (III)

where $R_5$ is a lower alkyl group having 1 to 4 carbon atoms; and $R_6$, $R_7$ and $R_8$ may be the same or different and each represents a hydrogen atom, a hydroxyl group, a methoxy group or an acetoxy group; and Compound IV represented by general formula (IV) below:

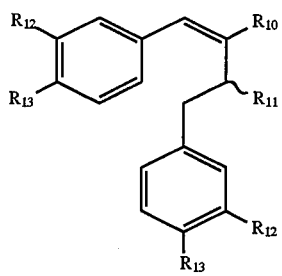 (IV)

where $R_{10}$ and $R_{11}$ may be the same or different and each represents a lower alkyl group having to 4 carbon atoms; and $R_{12}$ and $R_{13}$ may be the same or different and each represents a hydroxyl group or a methoxy group.

2. An angiogenesis inhibitor comprising, as an active ingredient, compound I represented by general formula (I) below:

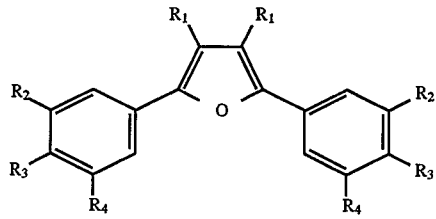 (I)

where $R_1$ represents a lower alkyl group having 1 to 4 carbon atoms, an alkoxycarbonyl group having 1 to 4 carbon atoms in the alkoxy moiety or a carboxyl group;

$R_2$, $R_3$ and $R_4$ may be the same or different and each represents a hydrogen atom, a hydroxyl group, a methoxy group or an acetoxy group and wherein $R_2$ and $R_3$ may bind together to close a ring as shown in general formula (II) below:

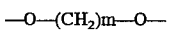 (II)

where m is an integer from 1 to 6.

3. An angiogenesis inhibitor comprising, as an active ingredient, compound III represented by the general formula (III) below:

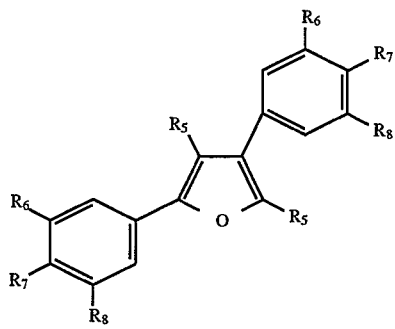 (III)

where $R_5$ is a lower alkyl group having 1 to 4 carbon atoms; and $R_6$, $R_7$ and $R_8$ may be the same or different and each represents a hydrogen atom, a hydroxyl group, a methoxy group or an acetoxy group.

4. An angiogenesis inhibitor comprising, as an active ingredient, a compound IV represented by general formula (IV) below:

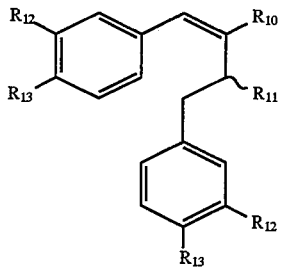 (IV)

where, $R_{10}$ and $R_{11}$ may be the same or different and each represents a lower alkyl group having 1 to 4 carbon atoms; and $R_{12}$ and $R_{13}$ may be the same or different and each represents a hydroxyl group or a methoxy group.

* * * * *